(12) United States Patent
Chen et al.

(10) Patent No.: US 11,952,368 B2
(45) Date of Patent: Apr. 9, 2024

(54) FAPI DIMER COMPOUND, FAPI DIMER-BASED POSITRON EMISSION TOMOGRAPHY (PET) IMAGING AGENT FOR TUMOR DIAGNOSIS, AND PREPARATION METHOD AND USE THEREOF

(71) Applicant: XIAMEN UNIVERSITY, Xiamen (CN)

(72) Inventors: Haojun Chen, Xiamen (CN); Liang Zhao, Xiamen (CN); Qin Lin, Xiamen (CN); Kaili Fu, Xiamen (CN); Yizhen Pang, Xiamen (CN); Zhide Guo, Xiamen (CN); Jianyang Fang, Xiamen (CN); Long Sun, Xiamen (CN); Hua Wu, Xiamen (CN)

(73) Assignee: Xiamen University, Xiamen (CN)

( * ) Notice: Subject to any disclaimer, the term of this patent is extended or adjusted under 35 U.S.C. 154(b) by 0 days.

(21) Appl. No.: 17/956,727

(22) Filed: Sep. 29, 2022

(65) Prior Publication Data
US 2023/0105190 A1    Apr. 6, 2023

(30) Foreign Application Priority Data
Sep. 29, 2021  (CN) .......................... 202111147651.X

(51) Int. Cl.
*C07D 401/14*  (2006.01)
*A61K 51/04*   (2006.01)

(52) U.S. Cl.
CPC ........ *C07D 401/14* (2013.01); *A61K 51/0482* (2013.01)

(58) Field of Classification Search
CPC .. C07D 401/14; C07D 401/00; C07D 215/00; A61K 51/0482; A61K 51/121
See application file for complete search history.

(56) References Cited

PUBLICATIONS

Zhao et al., "Development of Fibroblast Activation Protein Inhibitor-Based Dimeric Radiotracers with Improved Tumor Retention and Antitumor Efficacy," Aug. 2, 2022, Molecular Pharmaceutics</i>, vol. 19, pp. 3640-3651 (Year: 2022).*
Merriam-Webster, "Room temperature," Jul. 24, 2023, Merriam-Webster.com Dictionary (Year: 2023).*
Zhao et al., "Synthesis, Preclinical Evaluation, and a Pilot Clinical PET Imaging Study of 68Ga-Labeled FAPI Dimer," Sep. 23, 2021, The Journal of Nuclear Medicine, vol. 63, pp. 862-868 (Year: 2021).*

* cited by examiner

*Primary Examiner* — Jeffrey H Murray
*Assistant Examiner* — Madeline E Braun
(74) *Attorney, Agent, or Firm* — Reising Ethington P.C.

(57) ABSTRACT

Provided are a fibroblast activation protein inhibitor (FAPI) dimer compound, an FAPI dimer-based positron emission tomography (PET) imaging agent for tumor diagnosis, and a preparation method and use thereof. An amphiphilic polyethylene glycol (PEG) chain and a dimerized structure of FAPI in the FAPI dimer compound with a structure shown in formula I can improve the in vivo kinetic properties of the compound and prolong a residence time of the compound in a tumor, thereby improving the uptake and imaging effects in the tumor. The accurate tumor diagnosis can be achieved by labeling the FAPI dimer compound with a diagnostic nuclide ($^{68}$Ga), which has promising application prospects in PET imaging for diagnosis and in the preparation of a therapeutic nuclide (such as $^{177}$Lu or $^{90}$Y)-labeled drug for treating a FAP-α-expressing tumor.

6 Claims, 20 Drawing Sheets

FAPI DIMER COMPOUND, FAPI DIMER-BASED POSITRON EMISSION TOMOGRAPHY (PET) IMAGING AGENT FOR TUMOR DIAGNOSIS, AND PREPARATION METHOD AND USE THEREOF

TECHNICAL FIELD

The present disclosure relates to the technical field of medicine, and in particular to a fibroblast activation protein inhibitor (FAPI) dimer compound, an FAPI dimer-based positron emission tomography (PET) imaging agent for tumor diagnosis, and a preparation method and use thereof.

BACKGROUND

The early diagnosis, early treatment, and individualized comprehensive treatment of tumors is the most effective measure to reduce tumor mortality. Accurate imaging diagnosis, especially tumor molecular imaging, is one of the key links to realize the early diagnosis, early treatment, and individualized treatment of a tumor. Among various molecular imaging diagnosis techniques, single-photon emission computed tomography (SPECT) and PET that are based on nuclear medicine and molecular imaging have been widely used as representatives in clinical practice. Through radionuclide tracing, PET and SPECT can sensitively and clearly display the molecular imaging features of a deep tissue in a patient, which brings hope for the early diagnosis, early treatment, and individualized comprehensive treatment of cancer patients.

It can be known through the continuous exploration of tumorigenesis mechanisms that the occurrence, development, and metastasis of a tumor are closely related to a tumor microenvironment (TME). A tumor is considered as a product of the constant interaction between tumor cells and surrounding supporting tissues thereof or between different cell types in a tumor stroma. Cancer-associated fibroblasts (CAFs) are an important part in a TME, and are present in almost solid tumors, with a proportion as high as 90% in some tumor stromal tissues. Clinical studies have shown that CAF is an important prognostic factor for breast cancer, gastric cancer, and liver cancer.

Fibroblast activation protein (FAP) is a key protein for CAFs, which is a 97-kDa cell surface glycoprotein with gelatinase and dipeptidyl peptidase (DPP) activities. In an entire solid tumor tissue, FAP-positive CAFs are mostly located at an edge of a tissue or infiltrated in the tumor tissue, and play an important role in tumor immunoregulation. FAP is not expressed or expressed at a low level in normal fibroblasts, and is only transiently present in a tissue at a healing wound or expressed in chronic inflammatory diseases such as liver cirrhosis, such that FAP has become an attractive target for studying tumor stromal cell biology and potential tumor therapeutic targets. In recent years, the research of FAP-targeted $^{68}$Ga-FAPI-46 PET/CT imaging in clinical tumor diagnosis has progressed rapidly. Although $^{68}$Ga-FAPI-46 can quickly enter a tumor, a residence time is relatively short, resulting in unsatisfactory uptake and imaging effects in tumors with low FAP expression.

SUMMARY

In view of this, the present disclosure is intended to provide an FAPI dimer compound, a FAPI dimer-based PET imaging agent for tumor diagnosis, and a preparation method and use thereof. The FAPI dimer-based PET imaging agent for tumor diagnosis provided by the present disclosure has a long residence time in a tumor and a prominent imaging effect.

To achieve the above purpose, the present disclosure provides the following technical solutions.

The present disclosure provides fibroblast activation protein inhibitor (FAPI) dimer compound with a structure shown in formula I:

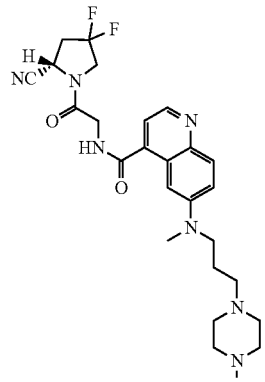

formula I

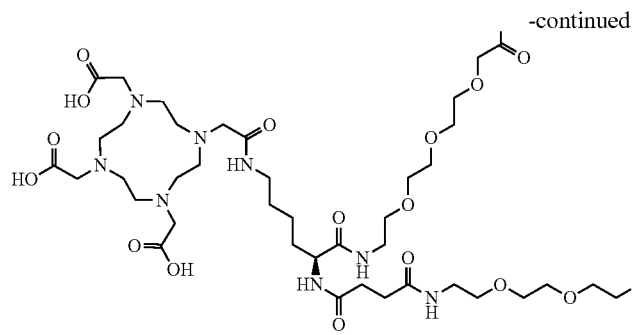

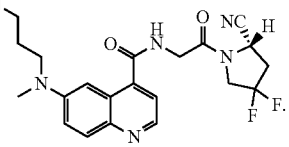

A preparation method of the above FAPI dimer compound includes the following steps:

(1) mixing a compound 1, a compound 2, a first condensation reagent, and a first organic base to allow a first condensation reaction, and subjecting a resulting condensation product to a first Boc protecting group removal reaction to obtain a compound 3;

(2) mixing the compound 3, a compound 4, a second condensation reagent, and a second organic base to allow a second condensation reaction, and subjecting a resulting condensation product to a second Boc protecting group removal reaction to obtain a compound 5;

(3) mixing the compound 5, a compound 6, a third condensation reagent, and a third organic base to allow a third condensation reaction, and subjecting a resulting condensation product to an Fmoc protecting group removal reaction to obtain a compound 7; and (4) mixing the compound 7, a compound 8, a fourth condensation reagent, and a fourth organic base to allow a fourth condensation reaction, and subjecting a resulting condensation product to a carboxylic acid protecting group removal reaction to obtain the FAPI dimer compound with a structure shown in formula I;

Compound 1

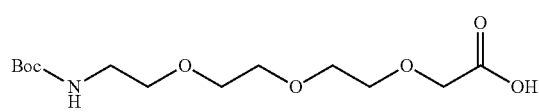

Compound 2

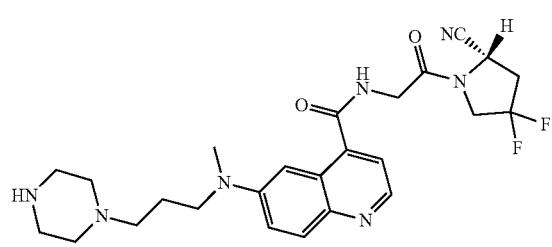

Compound 3

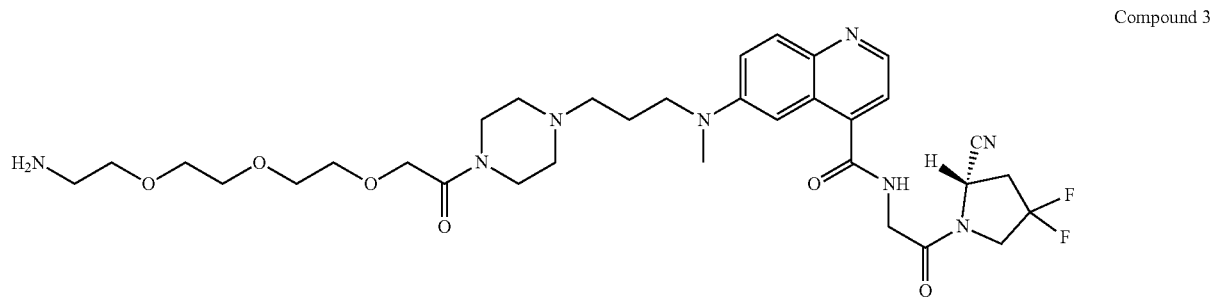

Compound 4
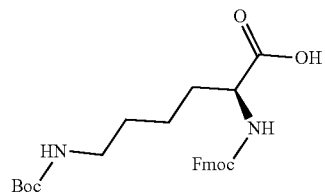
Compound 5
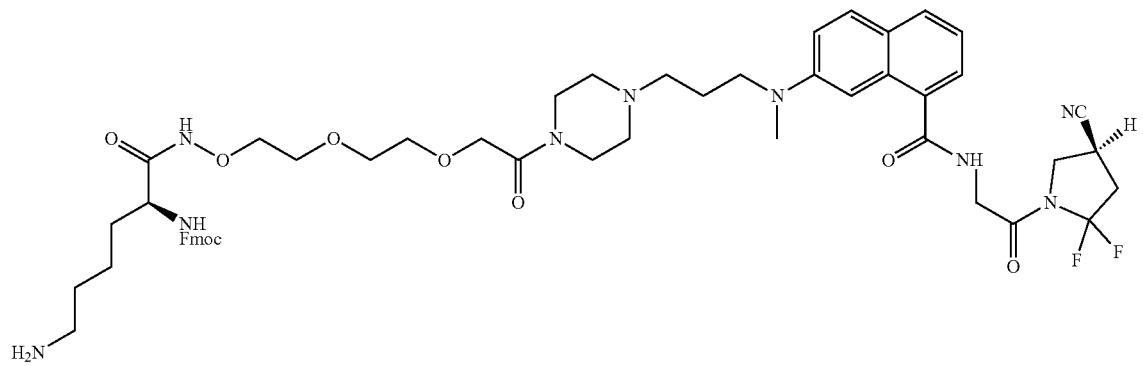
Compound 6
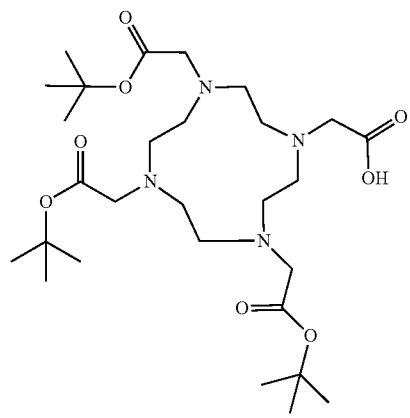
Compound 7
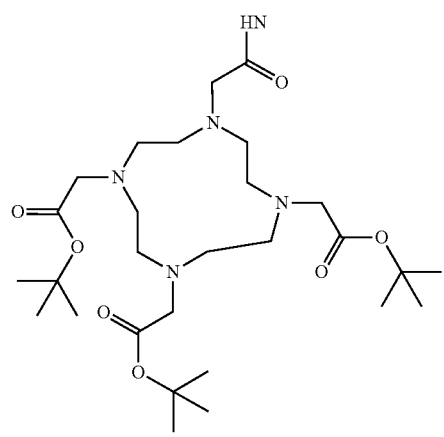

-continued

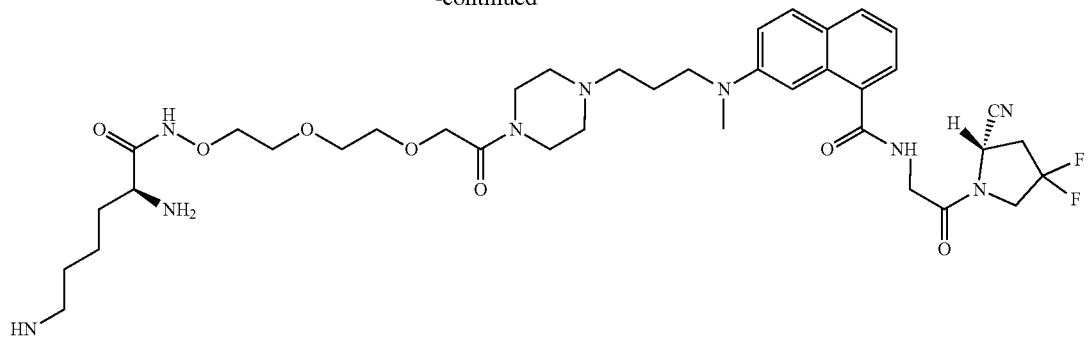

Compound 8

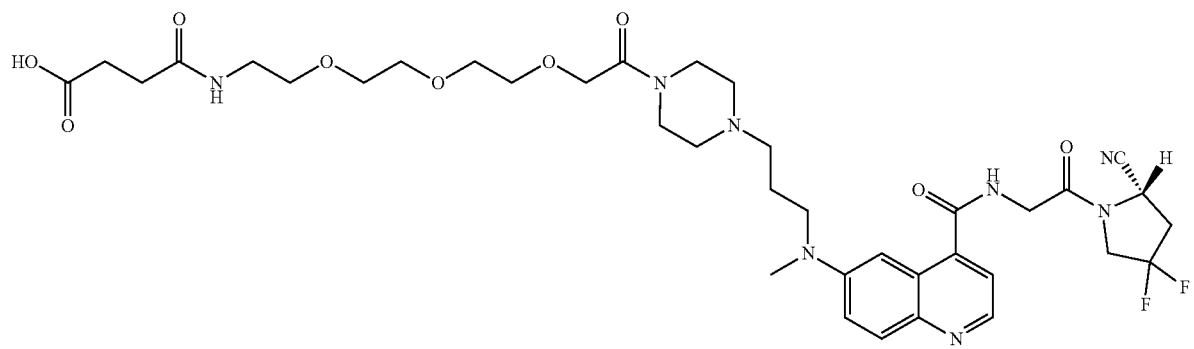

30

Preferably, in step (1), the compound 2, the compound 1, the first condensation reagent, and the first organic base are in a molar ratio of 1:(1-5):(1-5):(2-6);

the first condensation reaction is conducted at 25° C. to 100° C. for 4 h to 16 h; and the first Boc protecting group removal reaction is conducted at 0° C. to 50° C. for 0.5 h to 5 h.

Preferably, in step (2), the compound 3, the compound 4, the second condensation reagent, and the second organic base are in a molar ratio of 1:(1-5):(1-5):(2-6);

the second condensation reaction is conducted at 25° C. to 100° C. for 4 h to 16 h; and the second Boc protecting group removal reaction is conducted at 0° C. to 50° C. for 0.5 h to 3 h.

Preferably, in step (3), the compound 5, the compound 6, the third condensation reagent, and the third organic base are in a molar ratio of 1:(1-3):(2-6):(5-10);

the third condensation reaction is conducted at 25° C. to 100° C. for 4 h to 16 h; and the Fmoc protecting group removal reaction is conducted at 0° C. to 50° C. for 0.5 h to 3 h.

Preferably, in step (4), the compound 7, the compound 8, the fourth condensation reagent, and the fourth organic base are in a molar ratio of 1:(1-5):(2-6):(5-10);

the fourth condensation reaction is conducted at 25° C. to 100° C. for 1 h to 10 h; and the carboxylic acid protecting group removal reaction is conducted at 0° C. to 50° C. for 0.5 h to 5 h.

Preferably, the first condensation reagent, the second condensation reagent, the third condensation reagent, and the fourth condensation reagent each independently comprise one or more selected from the group consisting of 2-(7-azabenzotriazole)-N,N,N',N'-tetramethyluronium hexafluorophosphate (HATU), O—(N-succinimidyl)-N,N,N',N'-tetramethyluronium tetrafluoroborate (TSTU), and O-benzotriazole-tetramethyluronium hexafluorophosphate (HBTU); and the first organic base, the second organic base, the third organic base, and the fourth organic base each independently comprise an organic amine and/or 4-dimethylaminopyridine (4-DMAP).

An FAPI dimer-based positron emission tomography (PET) imaging agent for tumor diagnosis includes an FAPI dimer compound and a diagnostic nuclide, where the diagnostic nuclide comprises $^{68}$Ga and the FAPI dimer compound is the above FAPI dimer compound or an FAPI dimer compound prepared by the above preparation method.

A preparation method of the above FAPI dimer-based PET imaging agent for tumor diagnosis includes the following steps:

mixing the FAPI dimer compound with a diagnostic nuclide-containing solution to obtain a mixed solution, adjusting a pH of the mixed solution to 3.3 to 3.6, and radiolabeling to obtain the FAPI dimer-based PET imaging agent for tumor diagnosis.

The present disclosure further provides use of the above FAPI dimer compound, an FAPI dimer compound prepared by the above preparation method, the above FAPI dimer-based PET imaging agent for tumor diagnosis, or an FAPI dimer-based PET imaging agent for tumor diagnosis prepared by the above preparation method in PET imaging or in the preparation of a drug for diagnosing an FAP-α-expressing tumor.

The present disclosure provides an FAPI dimer compound with a structure shown in formula I. An amphiphilic polyethylene glycol (PEG) chain and a dimerized structure of FAPI in the FAPI dimer compound molecule provided by the present disclosure can improve the in vivo kinetic properties of the compound and prolong a residence time of the compound in a tumor. The FAPI dimer compound provided by the present disclosure is labeled with a diagnostic nuclide to obtain a PET imaging agent, such that the uptake and imaging effects of the PET imaging agent in a tumor can be improved, which has a promising application prospect in the diagnosis of an FAP-α-expressing tumor through PET imaging.

The present disclosure provides a preparation method of the FAPI dimer compound described in the above technical solution. The preparation method provided by the present disclosure involves a short reaction route, simple operations, cheap and easily-available raw materials, and a low production cost, and is suitable for industrial production.

The present disclosure provides an FAPI dimer-based PET imaging agent for tumor diagnosis, including an FAPI dimer compound and a diagnostic nuclide, where the diagnostic nuclide includes $^{68}$Ga and the FAPI dimer compound is the FAPI dimer compound described in the above technical solution or an FAPI dimer compound prepared by the preparation method described in the above technical solution. The FAPI dimer compound is used as a carrier in the PET imaging agent provided by the present disclosure. The FAPI dimer compound has a long residence time and high stability in a tumor, such that the PET imaging agent has excellent uptake and imaging effects in the tumor. The accurate diagnosis of a tumor can be achieved by labeling the FAPI dimer compound with a diagnostic nuclide, which has promising application prospects in PET imaging, in the preparation of a drug for diagnosing a FAP-α-expressing tumor, and in the preparation of a therapeutic nuclide (such as $^{177}$Lu or $^{90}$Y)-labeled drug for treating a FAP-α-expressing tumor. According to the results of examples, after the FAPI dimer-based PET imaging agent for tumor diagnosis provided by the present disclosure is co-incubated with phosphate-buffered saline (PBS) or fetal bovine serum (FBS) for 4 h, the $^{68}$Ga-2PEG(3)-FAPI-dimer is not significantly decomposed, and a radiochemical purity is greater than 90%, indicating that the $^{68}$Ga-2PEG(3)-FAPI-dimer prepared by the present disclosure has excellent stability. The binding of the $^{68}$Ga-2PEG(3)-FAPI-dimer prepared by the present disclosure to FAP is specific, and the 2PEG(3)-FAPI-dimer in the $^{68}$Ga-2PEG(3)-FAPI-dimer shows high binding affinity to a receptor and can be blocked by unlabeled FAPI-46, indicating that the $^{68}$Ga-2PEG(3)-FAPI-dimer prepared by the present disclosure exhibits prominent specificity in binding to FAP. In addition, the uptake of $^{68}$Ga-FAPI-46 is at a low level in a tumor lesion with low FAP expression (SUVmax 2.7), while the uptake of $^{68}$Ga-2PEG(3)-FAPI-dimer is at a high level in a corresponding lesion (SUVmax 9.8) (which is higher than that in surrounding liver tissues, resulting in a prominent target-to-background ratio), indicating that the $^{68}$Ga-2PEG(3)-FAPI-dimer prepared by the present disclosure has a better tumor uptake effect than $^{68}$Ga-FAPI-46 even in low-expression tumors.

The present disclosure provides a preparation method of the FAPI dimer-based PET imaging agent for tumor diagnosis described in the above technical solution. The preparation method provided by the present disclosure involves simple operations and a low production cost, and is suitable for industrial production.

BRIEF DESCRIPTION OF THE DRAWINGS

FIG. 5A shows the expression of FAP in a hepatocellular carcinoma (HCC) cell line Huh7 and CAFs, FIG. 5B shows the experimental results of cellular uptake and cellular uptake blockade of $^{68}$Ga-2PEG(3)-FAPI-dimer and $^{68}$Ga-FAPI-46 in CAFs, FIG. 5C shows the inhibition of unlabeled FAPI-46 on the binding of $^{68}$Ga-FAPI-46 to FAP on CAFs, and FIG. 5D shows the inhibition of unlabeled FAPI-46 on the binding of $^{68}$Ga-2PEG(3)-FAPI-dimer to FAP on CAFs;

FIG. 6A shows the immunohistochemical staining results and FIG. 6B shows the Western blotting results;

FIG. 7A shows representative static PET images of HCC-PDX-1 at 0.5 h, 1 h, 2 h, and 4 h after the $^{68}$Ga-2PEG(3)-FAPI-dimer and $^{68}$Ga-FAPI-46 are injected and FIG. 7B shows dynamic time-activity curves of $^{68}$Ga-2PEG(3)-FAPI-dimer in heart, kidney, liver, muscle, and tumor tissues;

FIG. 8A shows representative static PET images of HCC-PDX-2 at 0.5 h, 1 h, 2 h, and 4 h after the $^{68}$Ga-2PEG(3)-FAPI-dimer and $^{68}$Ga-FAPI-46 are injected and FIG. 8B shows representative static PET images of HCC-PDX-1 and HCC-PDX-2 that are administered with or without a competitive blocker and then injected with $^{68}$Ga-2PEG(3)-FAPI-dimer 1 h later;

FIG. 9A shows the in vitro biodistribution of $^{68}$Ga-FAPI-46 in HCC-PDX-1 at 1 h and 4 h after injection and FIG. 9B shows the in vitro biodistribution of $^{68}$Ga-2PEG(3)-FAPI-dimer in HCC-PDX-1 administered with or without unlabeled FAPI-46 as a blocker at 1 h and 4 h after injection;

FIG. 10A shows a PET image at 1 h after the $^{68}$Ga-FAPI-46 is injected, FIG. 10B shows a PET image at 1 h after the $^{68}$Ga-2PEG(3)-FAPI-dimer is injected, FIG. 10C shows a PET image at 4 h after the $^{68}$Ga-2PEG(3)-FAPI-dimer is injected, and FIG. 10D shows a hematoxylin and eosin (H&E) staining and FAP immunohistochemical staining result of metastatic lymph nodes obtained through puncture; FIG. 11A shows enhanced MRI images, FIG. 11B shows a computed tomography (CT) image and PET/CT images at 1 h after the $^{68}$Ga-FAPI-46 and $^{68}$Ga-2PEG(3)-FAPI-dimer are administered, and FIG. 11C shows surgical tissue, H&E staining, and FAP immunohistochemical staining results.

DETAILED DESCRIPTION OF THE EMBODIMENTS

Figure 1:
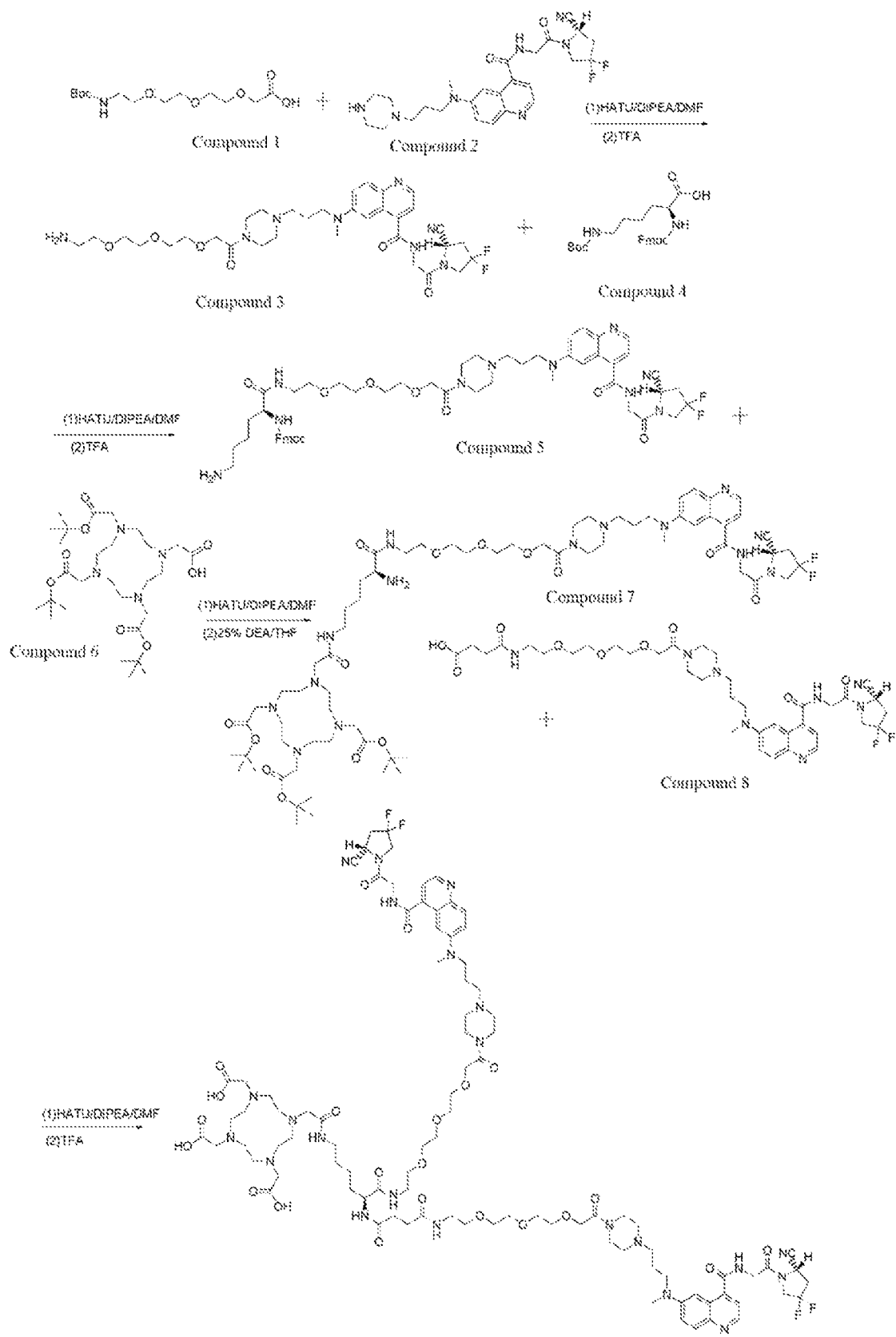
FIG. 1 shows a synthetic route of 2PEG(3)-FAPI-dimer.

The present disclosure provides an FAPI dimer compound with a structure shown in formula I:

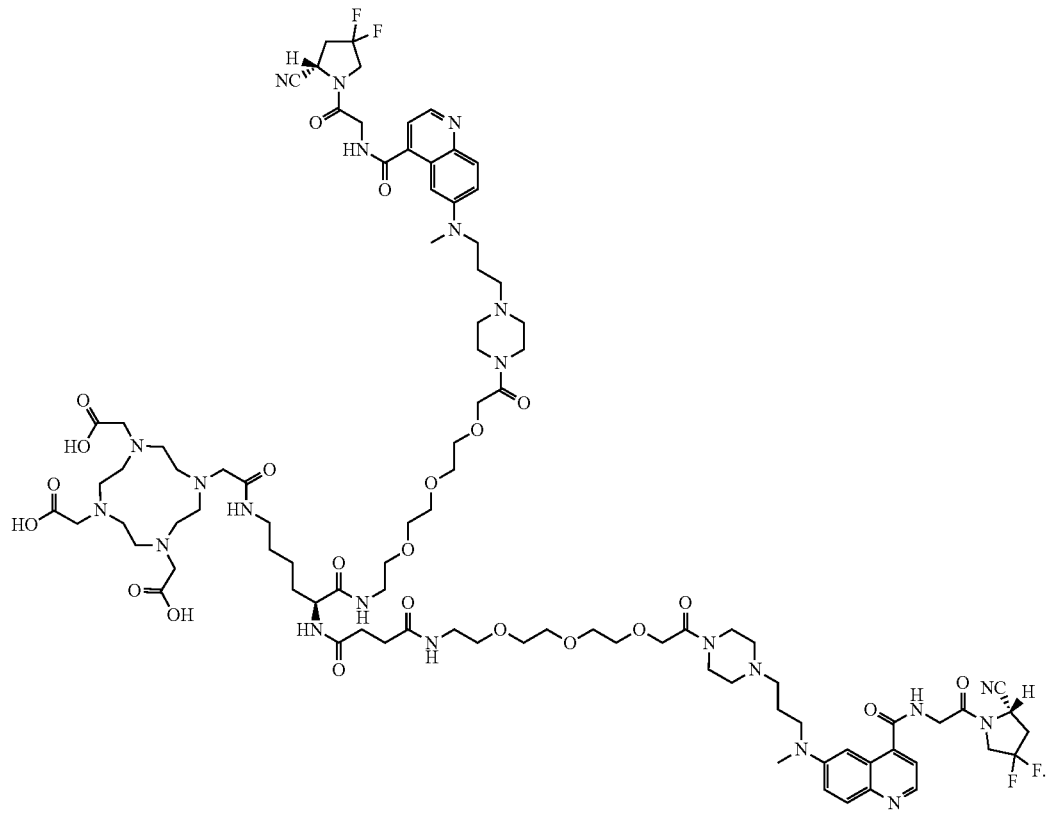

formula I

The present disclosure provides a preparation method of the FAPI dimer compound described in the above technical solution, including the following steps:

(1) mixing a compound 1, a compound 2, a first condensation reagent, and a first organic base to allow a first condensation reaction, and subjecting a resulting condensation product to a first Boc protecting group removal reaction to obtain a compound 3;

(2) mixing the compound 3, a compound 4, a second condensation reagent, and a second organic base to allow a second condensation reaction, and subjecting a resulting condensation product to a second Boc protecting group removal reaction to obtain a compound 5;

(3) mixing the compound 5, a compound 6, a third condensation reagent, and a third organic base to allow a third condensation reaction, and subjecting a resulting condensation product to an Fmoc protecting group removal reaction to obtain a compound 7; and (4) mixing the compound 7, a compound 8, a fourth condensation reagent, and a fourth organic base to allow a fourth condensation reaction, and subjecting a resulting condensation product to a carboxylic acid protecting group removal reaction to obtain the FAPI dimer compound with a structure shown in formula I;

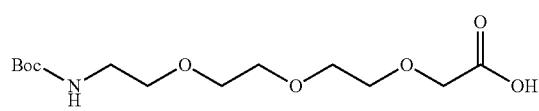

Compound 1

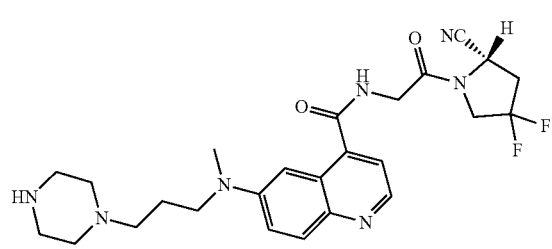

Compound 2

Compound 3
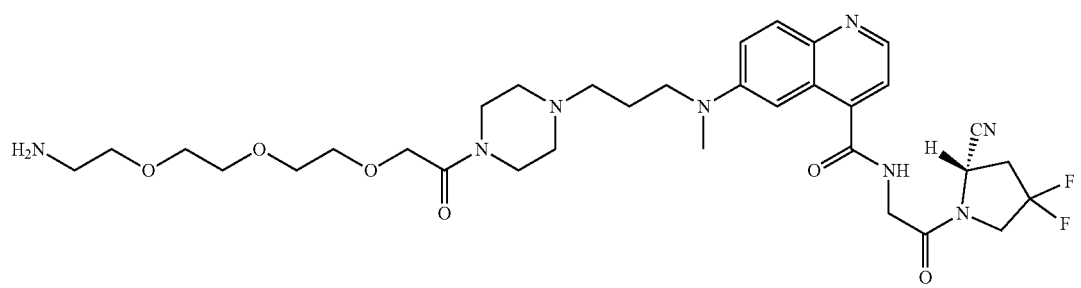
Compound 4
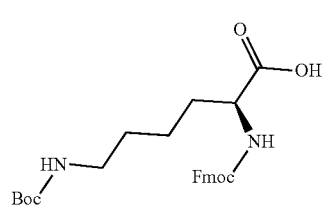
Compound 5
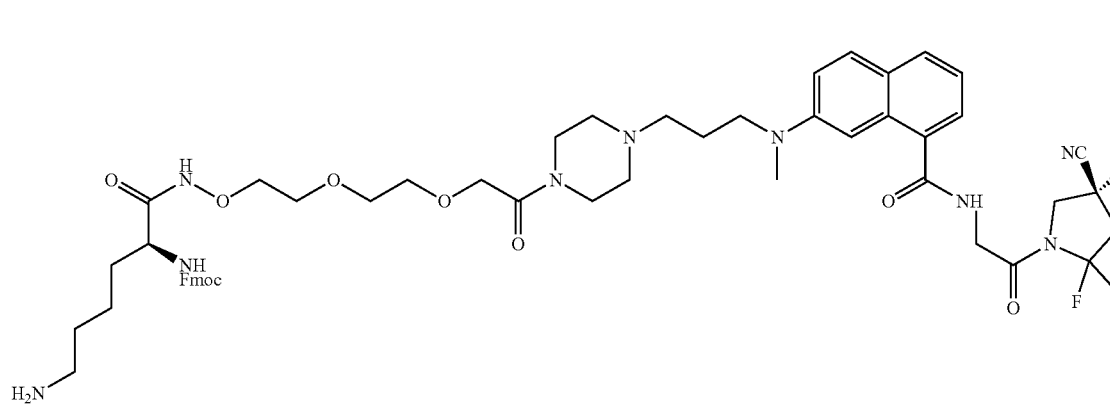
Compound 6
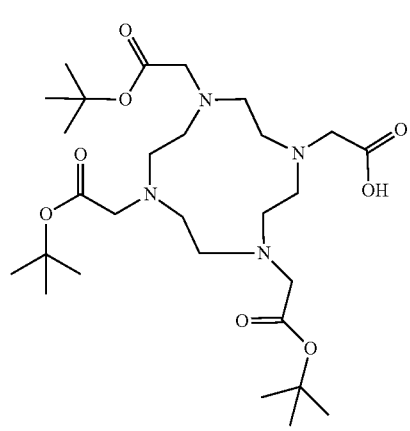

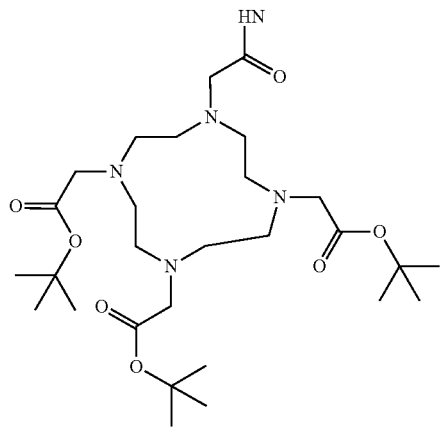

Compound 7

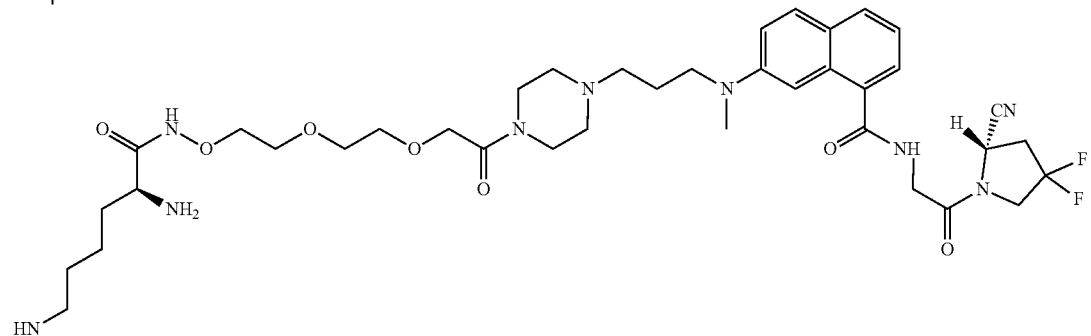

Compound 8

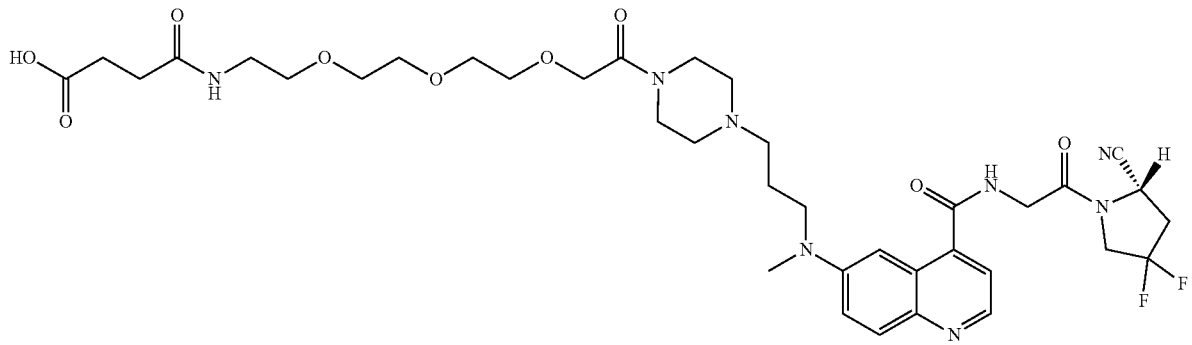

In the present disclosure, unless otherwise specified, all raw material components are commercially available products well known to those skilled in the art.

In the present disclosure, a compound 1, a compound 2, a first condensation reagent, and a first organic base are mixed to allow a first condensation reaction, and a resulting condensation product is subjected to a first Boc protecting group removal reaction to obtain a compound 3.

In the present disclosure, the first condensation reagent preferably includes one or more selected from the group consisting of 2-(7-azabenzotriazole)-N,N,N',N'-tetramethyluronium hexafluorophosphate (HATU), O—(N-succinimidyl)-N,N,N',N'-tetramethyluronium tetrafluoroborate (TSTU), and O-benzotriazole-tetramethyluronium hexafluorophosphate (HBTU); and when the first condensation reagent is a mixture of two or more selected from the group consisting of the above-mentioned substances, the present disclosure has no special limitation on a ratio of the two or more, and any ratio can be adopted. In the present disclosure, the first organic base preferably includes an organic amine and/or 4-dimethylaminopyridine (4-DMAP), and the organic amine preferably includes N,N-diisopropylethylamine (DIPEA) and/or triethylamine (TEA); and when the organic base is a mixture of two or more selected from the group consisting of the above-mentioned substances, the present disclosure has no special limitation on a ratio of the two or more, and any ratio can be adopted. In the present disclosure, the compound 2, the compound 1, the first condensation reagent, and the first organic base are in a molar ratio of preferably 1:(1-5):(1-5):(2-6), more preferably 1:(2-4):(2-4):(3-5), and further more preferably 1:3:3:4.

In the present disclosure, an organic solvent used for the first condensation reaction preferably includes one or more selected from the group consisting of N,N-dimethylformamide (DMF), tetrahydrofuran (THF), and dimethylsulfoxide (DMSO). The present disclosure has no special limitation on an amount of the organic solvent, as long as the first condensation reaction can proceed smoothly. In an embodiment of the present disclosure, a ratio of a molar mass of the compound 2 to a volume of the organic solvent is preferably 1 mmol:(3-10) mL and more preferably 1 mmol:(5-8) mL.

In the present disclosure, the first condensation reaction is conducted at a temperature of preferably 25° C. to 100° C. and more preferably 50° C. to 80° C.; and the first condensation reaction is conducted for preferably 4 h to 16 h and more preferably 5 h to 15 h. In the present disclosure, the first Boc protecting group removal reaction is preferably conducted under an acidic condition, and specifically, under an ice-water bath, an acid is added to the condensation product to allow the first Boc protecting group removal reaction; the acid preferably includes TFA and/or a hydrochloric acid solution; a solvent in the hydrochloric acid solution is preferably an alcohol, and the alcohol preferably includes methanol and/or ethanol; the hydrochloric acid solution has a concentration of preferably 0.5 mol/L to 2 mol/L; the acid is preferably added dropwise, and the present disclosure has no special limitation on a speed of the dropwise addition, as long as the dropwise addition can be achieved; a molar ratio of the compound 2 to the acid is preferably 1:(10-20) and more preferably 1:(15-18); the first Boc protecting group removal reaction is conducted at a temperature of preferably 0° C. to 50° C. and more preferably 10° C. to 20° C.; and the first Boc protecting group removal reaction is conducted for preferably 0.5 h to 5 h and more preferably 1 h to 2 h. In the present disclosure, specific reactions occurring during the first condensation reaction and the first Boc protecting group removal reaction are shown in FIG. 1.

After the first Boc protecting group removal reaction is completed, the present disclosure preferably further includes post-treatment, and the post-treatment includes: adjusting a pH of a reaction solution obtained after the first Boc protecting group removal reaction to 4.5 to 6.5, and purifying through HPLC to obtain a compound 3. In the present disclosure, an alkali used for the pH adjustment preferably includes sodium hydroxide or potassium hydroxide; and the alkali is preferably used in the form of a solid or a solution. The present disclosure has no special limitation on a concentration of the alkali solution, as long as the pH can be adjusted to 4.5 to 6.5. The pH is further preferably 5 to 5.5. In the present disclosure, the HPLC is preferably preparative HPLC; and the HPLC for purification is conducted preferably under the following conditions: mobile phase A: 0.1% TFA-acetonitrile, mobile phase B: 0.1% TFA-water, and elution mode: gradient elution for 0 min to 25 min, where a volume fraction of the mobile phase A is increased from 10% to 90%, and the mobile phase A and the mobile phase B both have a flow rate of 5 mL/min.

In the present disclosure, after the compound 3 is obtained, the compound 3, a compound 4, a second condensation reagent, and a second organic base are mixed to allow a second condensation reaction, and a resulting condensation product is subjected to a second Boc protecting group removal reaction to obtain a compound 5.

In the present disclosure, the optional types of the second condensation reagent and the second organic base are preferably the same as the optional types of the first condensation reagent and the first organic base, which will not be repeated here. In the present disclosure, the compound 3, the compound 4, the second condensation reagent, and the second organic base are in a molar ratio of preferably 1:(1-5):(1-5):(2-6), more preferably 1:(2-4):(2-4):(3-5), and further more preferably 1:3:3:4.

In the present disclosure, an organic solvent used for the second condensation reaction preferably includes one or more selected from the group consisting of DMF, THF, and DMSO. The present disclosure has no special limitation on an amount of the organic solvent, as long as the second condensation reaction can proceed smoothly. In an embodiment of the present disclosure, a ratio of a molar mass of the compound 3 to a volume of the organic solvent is preferably 1 mmol:(3-10) mL and more preferably 1 mmol:(5-8) mL.

In the present disclosure, the second condensation reaction is conducted at a temperature of preferably 25° C. to 100° C. and more preferably 50° C. to 80° C.; and the second condensation reaction is conducted for preferably 4 h to 16 h and more preferably 5 h to 15 h. In the present disclosure, the second Boc protecting group removal reaction is preferably conducted under an acidic condition, and specifically, under an ice-water bath, an acid is added to the condensation product to allow the second Boc protecting group removal reaction; the acid preferably includes TFA and/or a hydrochloric acid solution; a solvent in the hydrochloric acid solution is preferably an alcohol, and the alcohol preferably includes methanol and/or ethanol; the hydrochloric acid solution has a concentration of preferably 0.5 mol/L to 2 mol/L; the acid is preferably added dropwise, and the present disclosure has no special limitation on a speed of the dropwise addition, as long as the dropwise addition can be achieved; a molar ratio of the compound 3 to the acid is preferably 1:(10-20) and more preferably 1:(15-18); the second Boc protecting group removal reaction is conducted at a temperature of preferably 0° C. to 50° C. and more preferably 10° C. to 20° C.; and the second Boc protecting group removal reaction is conducted for preferably 0.5 h to 3 h and more preferably 1 h to 2 h. In the present disclosure, specific reactions occurring during the second condensation reaction and the second Boc protecting group removal reaction are shown in FIG. 1.

After the second Boc protecting group removal reaction is completed, the present disclosure preferably further includes post-treatment, and the post-treatment includes: adjusting a pH of a reaction solution obtained after the second Boc protecting group removal reaction to 4.5 to 6.5, and purifying through HPLC to obtain a compound 5. In the present disclosure, an alkali used for the pH adjustment preferably includes sodium hydroxide or potassium hydroxide; and the alkali is preferably used in the form of a solid or a solution. The present disclosure has no special limitation on a concentration of the alkali solution, as long as the pH can be adjusted to 4.5 to 6.5. The pH is further preferably 5 to 5.5. In the present disclosure, the HPLC is preferably preparative HPLC; and the HPLC for purification is conducted preferably under the following conditions: mobile phase A: 0.1% TFA-acetonitrile, mobile phase B: 0.1% TFA-water, and elution mode: gradient elution for 0 min to 25 min, where a volume fraction of the mobile phase A is increased from 10% to 90%, and the mobile phase A and the mobile phase B both have a flow rate of 5 mL/min.

In the present disclosure, after the compound 5 is obtained, the compound 5, a compound 6, a third condensation reagent, and a third organic base are mixed to allow a third condensation reaction, and a resulting condensation product is subjected to an Fmoc protecting group removal reaction to obtain a compound 7.

In the present disclosure, the optional types of the third condensation reagent and the third organic base are preferably the same as the optional types of the first condensation reagent and the first organic base, which will not be repeated here. In the present disclosure, the compound 5, the compound 6, the third condensation reagent, and the third organic base are in a molar ratio of preferably 1:(1-3):(2-6):(5-10), more preferably 1:(3-5):(6-9):(6-9), and further more preferably 1:2:4:8.

In the present disclosure, an organic solvent used for the third condensation reaction preferably includes one or more selected from the group consisting of DMF, THF, and DMSO. The present disclosure has no special limitation on an amount of the organic solvent, as long as the third condensation reaction can proceed smoothly. In an embodiment of the present disclosure, a ratio of a molar mass of the compound 5 to a volume of the organic solvent is preferably 1 mmol:(3-5) mL and more preferably 1 mmol:4 mL.

In the present disclosure, the third condensation reaction is conducted at a temperature of preferably 25° C. to 100° C. and more preferably 50° C. to 80° C.; and the third condensation reaction is conducted for preferably 4 h to 16 h and more preferably 5 h to 10 h. After the third condensation reaction is completed, the present disclosure preferably further includes subjecting a reaction solution obtained after the third condensation reaction to concentration and then an Fmoc protecting group removal reaction. The present disclosure has no special limitation on a manner of the concentration, as long as the organic solvent in the reaction solution can be removed.

In the present disclosure, the Fmoc protecting group removal reaction is preferably conducted in a diethanolamine-trifluoroacetic acid (DEA-TFA) mixed reagent, and specifically, under an ice-water bath, the DEA-TFA mixed reagent is added to the condensation product to allow an Fmoc protecting group removal reaction; in the DEA-TFA mixed reagent, a concentration of DEA is preferably 10 wt % to 30 wt % and more preferably 20 wt % to 25 wt %; a ratio of a molar mass of the compound 5 to a volume of the DEA-TFA mixed reagent is preferably 1 mmol:(0.5-3) mL and more preferably 1 mmol:(1-2) mL; the DEA-TFA mixed reagent is preferably added dropwise, and the present disclosure has no special limitation on a speed of the dropwise addition, as long as the dropwise addition can be achieved; the Fmoc protecting group removal reaction is conducted at a temperature of preferably 0° C. to 50° C. and more preferably 10° C. to 20° C.; and the Fmoc protecting group removal reaction is conducted for preferably 0.5 h to 3 h and more preferably 1 h to 2 h. In the present disclosure, specific reactions occurring during the third condensation reaction and Fmoc protecting group removal reaction are shown in FIG. 1.

After the Fmoc protecting group removal reaction is completed, the present disclosure preferably further includes post-treatment, and the post-treatment includes: adjusting a pH of a reaction solution obtained after the Fmoc protecting group removal reaction to 4.5 to 6.5, and purifying through HPLC to obtain a compound 7. In the present disclosure, an alkali used for the pH adjustment preferably includes sodium hydroxide or potassium hydroxide; and the alkali is preferably used in the form of a solid or a solution. The present disclosure has no special limitation on a concentration of the alkali solution, as long as the pH can be adjusted to 4.5 to 6.5. The pH is further preferably 5 to 5.5. In the present disclosure, the HPLC is preferably preparative HPLC; and the HPLC for purification is conducted preferably under the following conditions: mobile phase A: 0.1% TFA-acetonitrile, mobile phase B: 0.1% TFA-water, and elution mode: gradient elution for 0 min to 25 min, where a volume fraction of the mobile phase A is increased from 10% to 90%, and the mobile phase A and the mobile phase B both have a flow rate of 5 mL/min.

In the present disclosure, after the compound 7 is obtained, the compound 7, a compound 8, a fourth condensation reagent, and a fourth organic base are mixed to allow a fourth condensation reaction, and a resulting condensation product is subjected to a carboxylic acid protecting group removal reaction to obtain the FAPI dimer compound with a structure shown in formula I.

In the present disclosure, the optional types of the fourth condensation reagent and the fourth organic base are preferably the same as the optional types of the first condensation reagent and the first organic base, which will not be repeated here. In the present disclosure, the compound 5, the compound 6, the third condensation reagent, and the third organic base are in a molar ratio of preferably 1:(1-3):(2-6):(5-10), more preferably 1:(3-5):(6-9):(6-9), and further more preferably 1:2:4:8.

In the present disclosure, an organic solvent used for the fourth condensation reaction preferably includes one or more selected from the group consisting of DMF, THF, and DMSO. The present disclosure has no special limitation on an amount of the organic solvent, as long as the fourth condensation reaction can proceed smoothly. In an embodiment of the present disclosure, a ratio of a molar mass of the compound 5 to a volume of the organic solvent is preferably 1 mmol:(3-5) mL and more preferably 1 mmol:4 mL.

In the present disclosure, the fourth condensation reaction is conducted at a temperature of preferably 25° C. to 100° C. and more preferably 50° C. to 80° C.; and the fourth condensation reaction is conducted for preferably 1 h to 10 h and more preferably 5 h to 8 h. In the present disclosure, the carboxylic acid protecting group removal reaction is preferably conducted under an acidic condition, and specifically, under an ice-water bath, an acid is added to the condensation product to allow the carboxylic acid protecting group removal reaction; the acid preferably includes TFA and/or a hydrochloric acid solution; a solvent in the hydrochloric acid solution is preferably an alcohol, and the alcohol preferably includes methanol and/or ethanol; the hydrochloric acid solution has a concentration of preferably 0.5 mol/L to 2 mol/L; the acid is preferably added dropwise, and the present disclosure has no special limitation on a speed of the dropwise addition, as long as the dropwise addition can be achieved; a molar ratio of the compound 2 to the acid is preferably 1:(10-20) and more preferably 1:(15-18); the carboxylic acid protecting group removal reaction is conducted at a temperature of preferably 0° C. to 50° C. and more preferably 10° C. to 20° C.; and the carboxylic acid protecting group removal reaction is conducted for preferably 0.5 h to 5 h and more preferably 1 h to 2 h. In the present disclosure, specific reactions occurring during the fourth condensation reaction and carboxylic acid protecting group removal reaction are shown in FIG. 1.

After the carboxylic acid protecting group removal reaction is completed, the present disclosure preferably further includes post-treatment, and the post-treatment includes: adjusting a pH of a reaction solution obtained after the carboxylic acid protecting group removal reaction to 5.5, and purifying through HPLC to obtain the FAPI dimer compound with a structure shown in formula I. In the present disclosure, an alkali used for the pH adjustment to 5.5 preferably includes sodium hydroxide or potassium hydroxide; and the alkali is preferably used in the form of a solid or a solution. The present disclosure has no special limitation on a concentration of the alkali solution, as long as the pH can be adjusted to 5.5. In the present disclosure, the HPLC is preferably preparative HPLC; and the HPLC for purification is conducted preferably under the following conditions: mobile phase A: 0.1% TFA-acetonitrile, mobile phase B: 0.1% TFA-water, and elution mode: gradient elution for 0 min to 25 min, where a volume fraction of the mobile phase A is increased from 10% to 90%, and the mobile phase A and the mobile phase B both have a flow rate of 5 mL/min.

The present disclosure provides an FAPI dimer-based PET imaging agent for tumor diagnosis, including an FAPI dimer compound and a diagnostic nuclide, where the diagnostic nuclide includes $^{68}$Ga and the FAPI dimer compound is the FAPI dimer compound described in the above technical solution or an FAPI dimer compound prepared by the preparation method described in the above technical solution.

In the present disclosure, in the FAPI dimer-based PET imaging agent for tumor diagnosis, an injection dose of the diagnostic nuclide is preferably 1.5 MBq/kg to 3.7 MBq/kg and more preferably 1.85 MBq/kg to 2.96 MBq/kg.

The present disclosure provides a preparation method of the FAPI dimer-based PET imaging agent for tumor diagnosis described in the above technical solution, including the following steps:

mixing the FAPI dimer compound with a diagnostic nuclide-containing solution to obtain a mixed solution, adjusting a pH of the mixed solution to 3.3 to 3.6, and radiolabeling to obtain the FAPI dimer-based PET imaging agent for tumor diagnosis.

In the present disclosure, the diagnostic nuclide-containing solution includes a diagnostic nuclide and a hydrochloric acid aqueous solution, where a concentration of the diagnostic nuclide is preferably 296 MBq/mL to 333 MBq/mL and the hydrochloric acid aqueous solution has a concentration of preferably 0.1 mol/L to 1 mol/L and more preferably 0.5 mol/L to 0.6 mol/L.

In the present disclosure, a specific activity of the diagnostic nuclide in the FAPI dimer compound and the diagnostic nuclide-containing solution is preferably 10 GBq/μmol to 40 GBq/μmol and more preferably 15 GBq/μmol to 37 GBq/μmol.

In the present disclosure, a pH adjusting agent used for the pH adjustment of the mixed solution preferably includes sodium acetate and/or hydrochloric acid; and the pH adjusting agent is preferably used in the form of an aqueous solution, and the pH adjusting agent aqueous solution has a concentration of preferably 1 mol/L to 3 mol/L and more preferably 2 mol/L to 2.5 mol/L. The present disclosure has no special limitation on an amount of the pH adjusting agent, as long as the pH can be adjusted to 3.3 to 3.6. The pH is preferably 3.4 to 3.5.

In the present disclosure, the radiolabeling is conducted at a temperature of preferably 50° C. to 150° C. and more preferably 85° C. to 100° C.; and the radiolabeling is conducted for preferably 5 min to 30 min and more preferably 10 min to 15 min. In the present disclosure, with $^{68}$Ga as an example, a reaction occurring during a radiolabeling process is as follows:

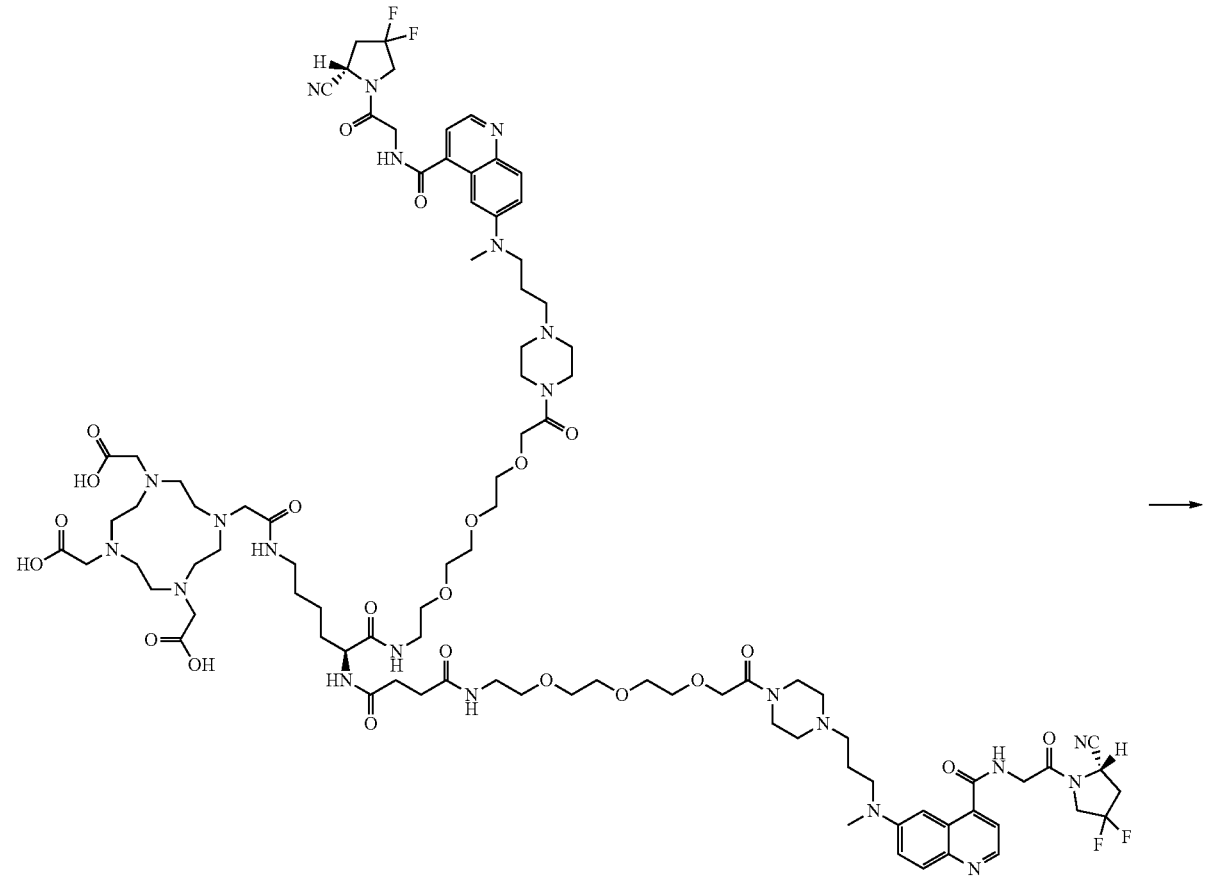

-continued

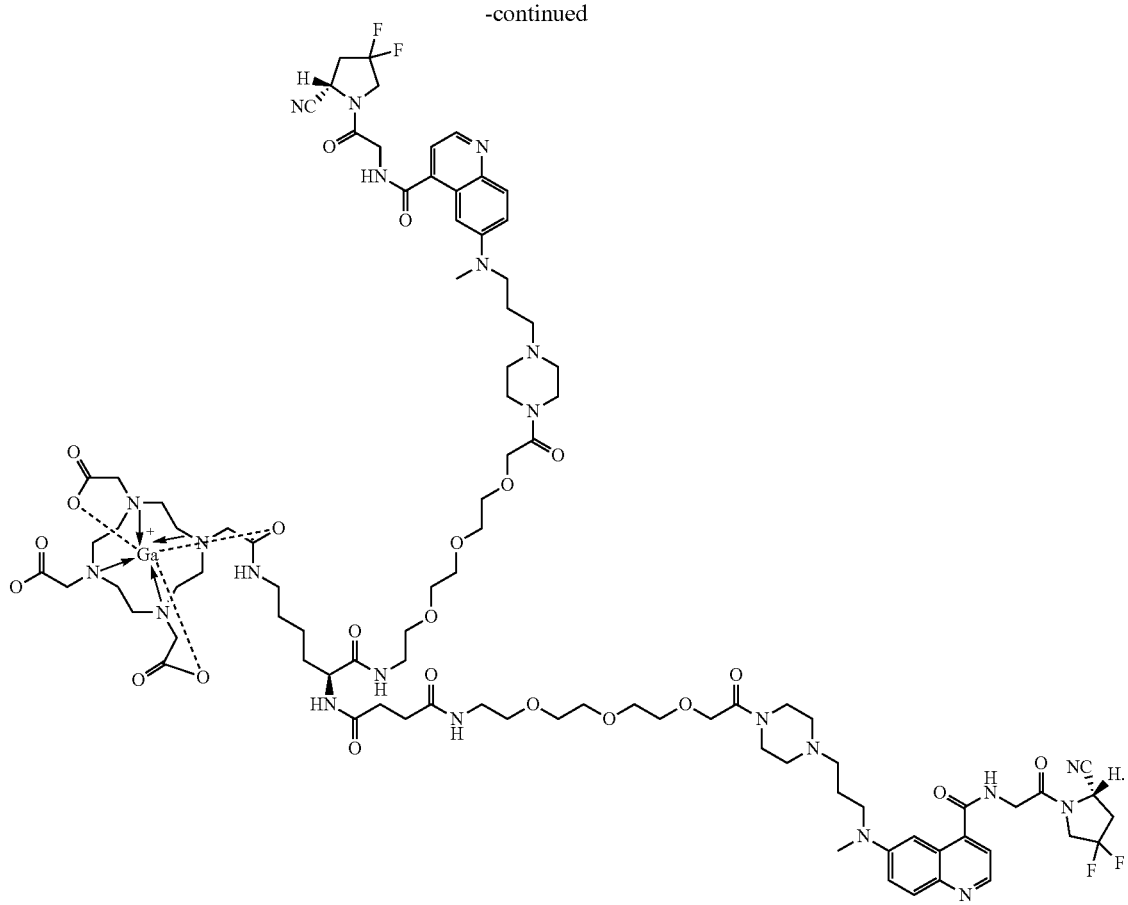

After the radiolabeling, the present disclosure preferably further includes subjecting a system obtained after the radiolabeling to separation through HPLC to obtain the FAPI dimer-based PET imaging agent for tumor diagnosis. In the present disclosure, a chromatographic column used for the separation through HPLC is preferably a C18 Sep-Pak column (WAT020515, Waters, USA); and an eluent used for the separation through HPLC is preferably an alcohol solvent, and the alcohol solvent is preferably ethanol.

The present disclosure provides use of the FAPI dimer compound described in the above technical solution, an FAPI dimer compound prepared by the preparation method described in the above technical solution, the FAPI dimer-based PET imaging agent for tumor diagnosis described in the above technical solution, or an FAPI dimer-based PET imaging agent for tumor diagnosis prepared by the preparation method described in the above technical solution in PET imaging or in the preparation of a drug for diagnosing an FAP-α-expressing tumor.

The technical solutions of the present disclosure will be clearly and completely described below in conjunction with the examples of the present disclosure. Apparently, the described examples are merely some rather than all of the examples of the present disclosure. All other examples obtained by a person of ordinary skill in the art based on the examples of the present disclosure without creative efforts shall fall within the protection scope of the present disclosure.

EXAMPLE 1

(1) Synthesis of a Compound 3

A compound 2 (500 mg, 1 mmol) and a compound 1 (Boc-PEG3-OH, 338 mg, 1.1 mmol) were dissolved in 3 mL of DMF, HATU (570 mg, 1.5 mmol) and DIPEA (710 mg, 5.5 mmol) were added, and a resulting mixture was stirred at 80° C. to allow a first condensation reaction for 16 h; a resulting reaction solution was transferred to an ice bath, and TFA (1.15 mL, 15 mmol) was added dropwise to allow a first Boc protecting group removal reaction for 3 h at room temperature under stirring; and a pH was adjusted with a NaOH solution (concentration: 1 mol/L) to 5.5, and purification was conducted through preparative HPLC to obtain the compound 3 (200 mg, purity: 95%). The preparative HPLC for purification was conducted under the following conditions: mobile phase A: 0.1% TFA-acetonitrile, mobile phase B: 0.1% TFA-water, and elution mode: gradient elution for 0 min to 25 min, where a volume fraction of the mobile phase A was increased from 10% to 90%, and the mobile phase A and the mobile phase B both had a flow rate of 5 mL/min. LC-MS (ESI$^+$) of the compound 2: m/z 689.6 [M+H]$^+$, 345.4 [M+2H]$^+$/2.

(2) Synthesis of a Compound 5

The compound 3 (68.9 mg, 0.1 mmol) and a compound 4 (56 mg, 1.1 mmol) were dissolved in 1 mL of DMF, HATU (57 mg, 0.15 mmol) and DIPEA (71 mg, 0.55 mmol) were added, and a resulting mixture was stirred at 80° C. to allow a second condensation reaction for 8 h; a resulting reaction solution was transferred to an ice bath, and TFA (0.2 mL, 1.8 mmol) was added dropwise to allow a second Boc protecting group removal reaction for 1 h at room temperature under stirring; and a pH was adjusted with a 1 M NaOH solution to 5.5, and purification was conducted through preparative HPLC to obtain the compound 5 (50 mg, purity: 95%). The preparative HPLC for purification was conducted under the following conditions: mobile phase A: 0.1% TFA-acetonitrile, mobile phase B: 0.1% TFA-water, and elution mode: gradient elution for 0 min to 25 min, where a volume fraction of the mobile phase A was increased from 10% to 90%, and the mobile phase A and the mobile phase B both had a flow rate of 5 mL/min. LC-MS (EST$^+$) of the compound 5: m/z 1039.9 [M+H]$^+$, 520.5 [M+2H]$^+$/2.

(3) Synthesis of a Compound 7

The compound 5 (30 mg, 0.028 mmol) and a compound 6 (20 mg, 0.035 mmol) were dissolved in 1.5 mL of DMF, HATU (16 mg, 0.042 mmol) and DIPEA (20 mg, 0.154 mmol) were added, and a resulting mixture was stirred at room temperature to allow a third condensation reaction for 6 h; DMF was removed through vacuum distillation, and 1 mL of a DEA-TFA mixed solution with a DEA concentration of 25 wt % was added dropwise to allow an Fmoc protecting group removal reaction for 1 h at room temperature under stirring; and purification was conducted through preparative HPLC to obtain the compound 7 (10 mg, purity: 95%). The preparative HPLC for purification was conducted under the following conditions: mobile phase A: 0.1% TFA-acetonitrile, mobile phase B: 0.1% TFA-water, and elution mode: gradient elution for 0 min to 25 min, where a volume fraction of the mobile phase A was increased from 10% to 90%, and the mobile phase A and the mobile phase B both had a flow rate of 5 mL/min. LC-MS (ESI$^+$) of the compound 7: m/z 686.8 [M+2H]$^+$/2.

(4) Synthesis of an FAPI Dimer Compound 2PEG(3)-FAPI-Dimer

The compound 7 (16 mg, 0.01 mmol) and a compound 8 (9.5 mg, 0.011 mmol) were dissolved in 1 mL of DMF, HATU (5.7 mg, 0.015 mmol) and DIPEA (7.1 mg, 0.055 mmol) were added, and a resulting mixture was stirred at 80° C. to allow a fourth condensation reaction for 4 h; a resulting reaction solution was transferred to an ice bath, and TFA (0.02 mL, 0.18 mmol) was added dropwise to allow a carboxylic acid protecting group removal reaction for 1 h at room temperature under stirring; and a pH was adjusted with a 5 mol/L NaOH solution to 5.5, and a resulting 2PEG(3)-FAPI-dimer-containing reaction solution was subjected to purification through preparative HPLC to obtain the FAPI dimer compound (abbreviated as 2PEG(3)-FAPI-dimer, 50 mg, purity: 95%). The preparative HPLC for purification was conducted under the following conditions: mobile phase A: 0.1% TFA-acetonitrile, mobile phase B: 0.1% TFA-water, and elution mode: gradient elution for 0 min to 25 min, where a volume fraction of the mobile phase A was increased from 10% to 90%, and the mobile phase A and the mobile phase B both had a flow rate of 5 mL/min. LC-MS (ESI$^+$) of 2PEG(3)-FAPI-dimer: m/z 659.3 [M+3H]$^+$/3.

(5) Synthesis of an FAPI Dimer-Based PET Imaging Agent for Tumor Diagnosis ($^{68}$Ga-2PEG(3)-FAPI-Dimer)

2PEG(3)-FAPI-dimer (50 μg, 25.3 nmol) was mixed with 4 mL of a $^{68}$Ga solution (1.3 GBq was dissolved in a 0.6 mol/L hydrochloric acid aqueous solution), 1 mL of a 2.5 mol/L sodium acetate aqueous solution was added to adjust a pH to 3.3 to 3.6, radiolabeling was conducted at 100° C. for 15 min, and then separation was conducted through HPLC to obtain the FAPI dimer-based PET imaging agent for tumor diagnosis (abbreviated as $^{68}$Ga-2PEG(3)-FAPI-dimer). For the HPLC separation, a C18 Sep-Pak chromatographic column (WAT020515, Waters, USA) was adopted, and 0.5 mL of ethanol was adopted as an eluent.

Figure 2:
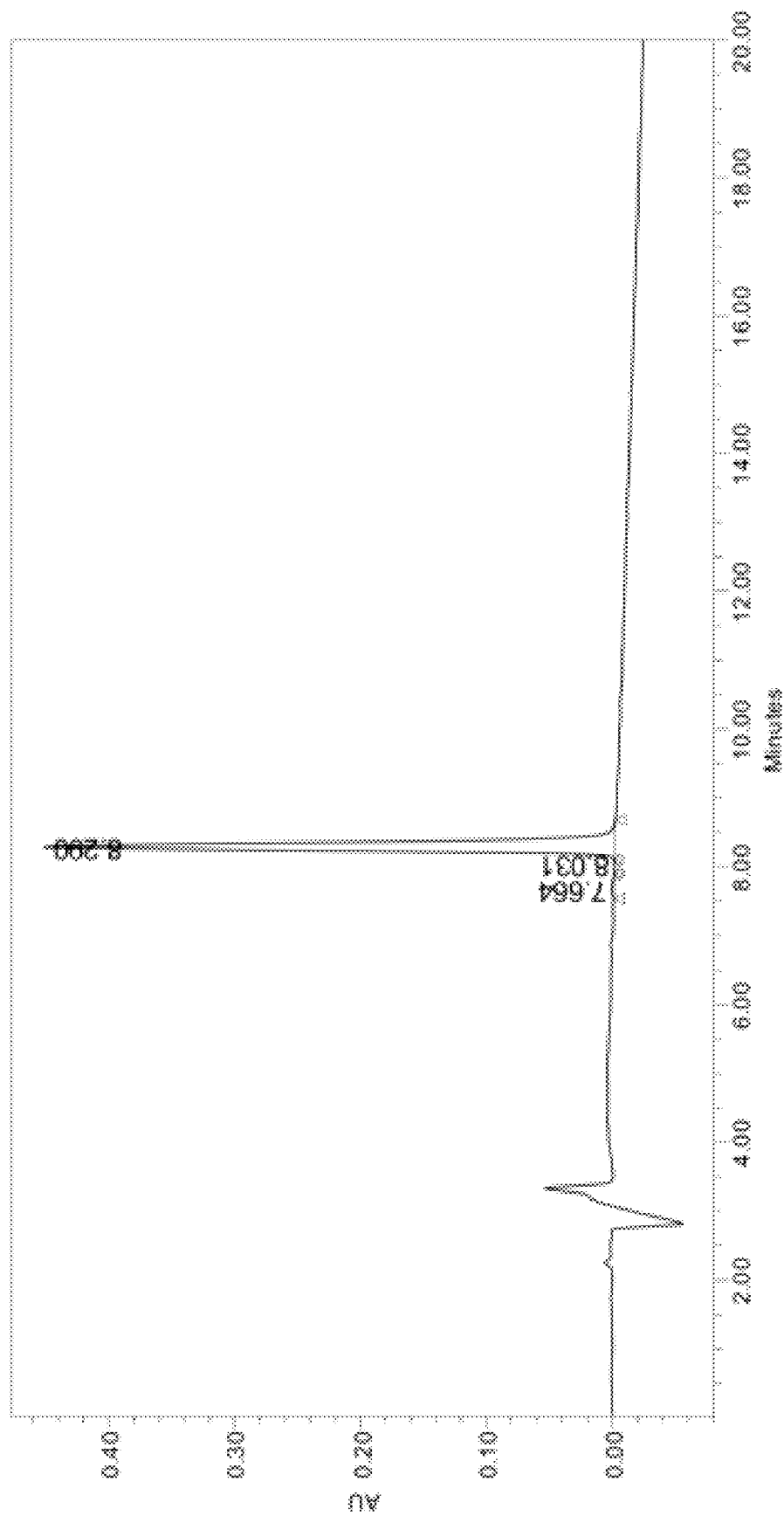
FIG. 2 shows an high-performance liquid chromatography (HPLC) analysis result of a 2PEG(3)-FAPI-dimer-containing reaction solution.

HPLC analysis results of a 2PEG(3)-FAPI-dimer-containing reaction solution in step (4) were shown in FIG. 2 and Table 1.

TABLE 1

HPLC analysis results of the 2PEG(3)-FAPI-dimer-containing reaction solution

| Retention time/min | Peak area | Peak height/% | Peak width (s) | Peak area/% |
|---|---|---|---|---|
| 7.664 | 16974 | 0.36 | 22.000 | 0.48 |
| 8.031 | 3271 | 0.10 | 12.000 | 0.09 |
| 8.290 | 3545868 | 99.54 | 35.000 | 99.43 |

It can be seen from Table 1 and FIG. 2 that a chemical purity of the target product (2PEG(3)-FAPI-dimer) is greater than 99%.

Figure 3:
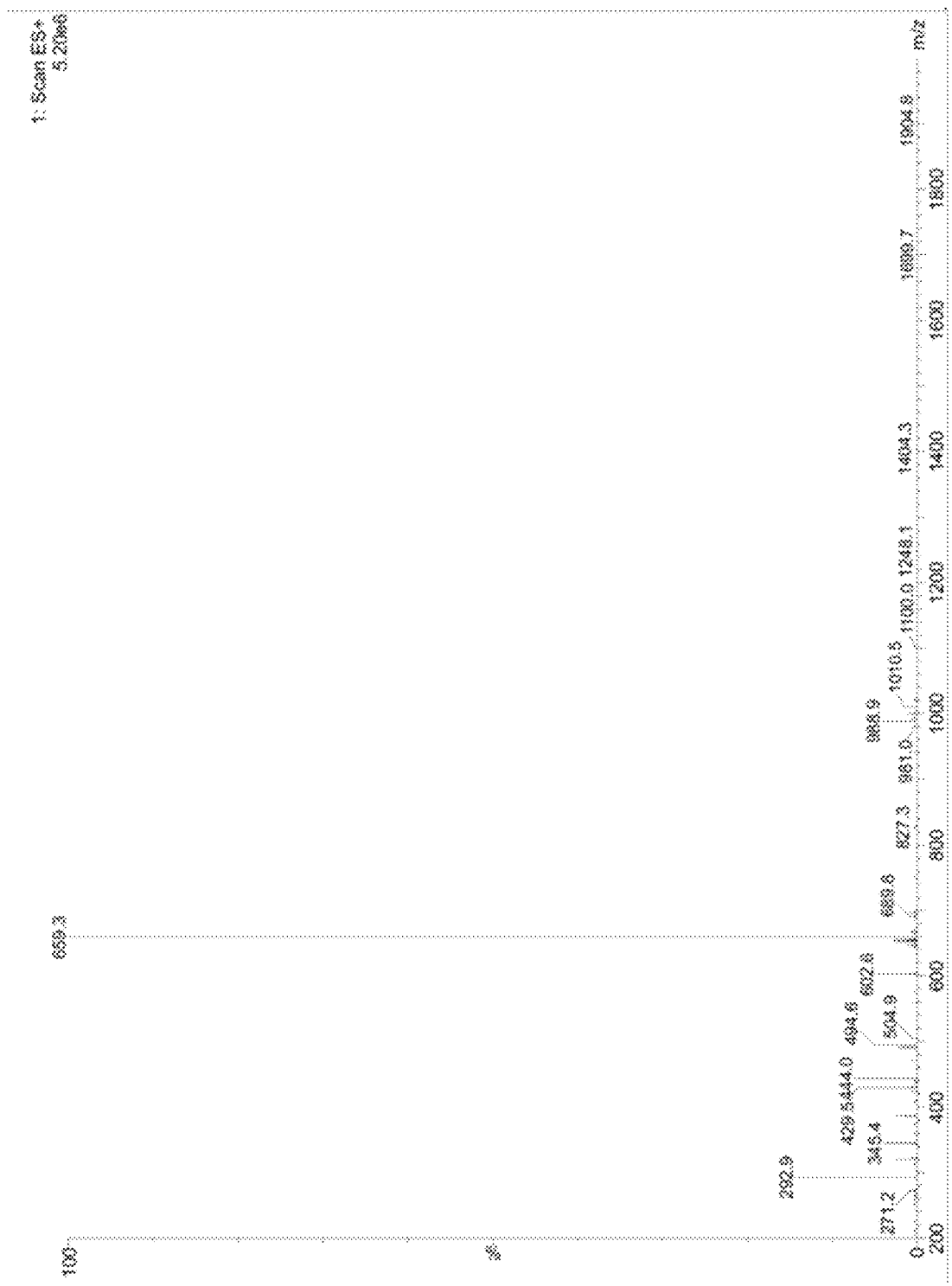
FIG. 3 shows a liquid chromatography-mass spectrometry (LC-MS) spectrum of 2PEG(3)-FAPI-dimer.

FIG. 3 shows an LC-MS spectrum of 2PEG(3)-FAPI-dimer, and it can be seen from FIG. 3 that the product 2PEG(3)-FAPI-dimer has a molecular weight of 659.3 [M+3H]$^+$/3 (namely, 1,974.19), which is the target product.

COMPARATIVE EXAMPLE 1

A compound in this comparative example was prepared according to the method in step (5) of Example 1 except that FAPI-46 was used instead of 2PEG(3)-FAPI-dimer to obtain $^{68}$Ga-FAPI-46, where the FAPI-46 was purchased from CS Bio (Shanghai) Co., Ltd.

TEST EXAMPLE 1

Stability Test

20 μL of a solution of the $^{68}$Ga-2PEG(3)-FAPI-dimer (3.7 MBq activity/20 μL) prepared in Example 1 (with normal saline (NS) as a solvent) was taken and added to a centrifuge tube with 100 μL of FBS, and incubated at 37° C. for 1 h, 2 h, and 4 h to obtain an FBS co-incubation solution; 20 μL of the FBS co-incubation solution was taken, 40 μL of acetonitrile was added for protein precipitation, and a resulting mixture was filtered through a 0.22 μm needle filter membrane; and a radiochemical purity was analyzed through HPLC. Test results were shown in FIG. 4.

20 μL of a solution of the $^{68}$Ga-2PEG(3)-FAPI-dimer (3.7 MBq activity/20 μL) prepared in Example 1 (with NS as a solvent) was taken and added to a centrifuge tube with 100 μL of PBS (pH=7.4), and incubated at 37° C. for 1 h, 2 h, and 4 h to obtain a PBS co-incubation solution; 20 μL of the PBS co-incubation solution was taken and filtered through a 0.22 μm needle filter membrane; and a radiochemical purity was analyzed through HPLC. Test results were shown in FIG. 4.

The HPLC analysis was conducted under the following conditions: C18 column (250×4.6 mm, 5 μm, Thermo); mobile phase A: water+0.1% TFA; mobile phase B: acetonitrile+0.1% TFA; gradient elution: 0 min to 25 min; mobile phase B with a volume fraction of 5% to 95%: 25 min to 30 min; mobile phase B with a volume fraction of 95%: 30 min to 40 min; and mobile phase B with a volume fraction of 5%; where the mobile phase A and the mobile phase B both had a flow rate of 1 mL/min.

Figure 4:
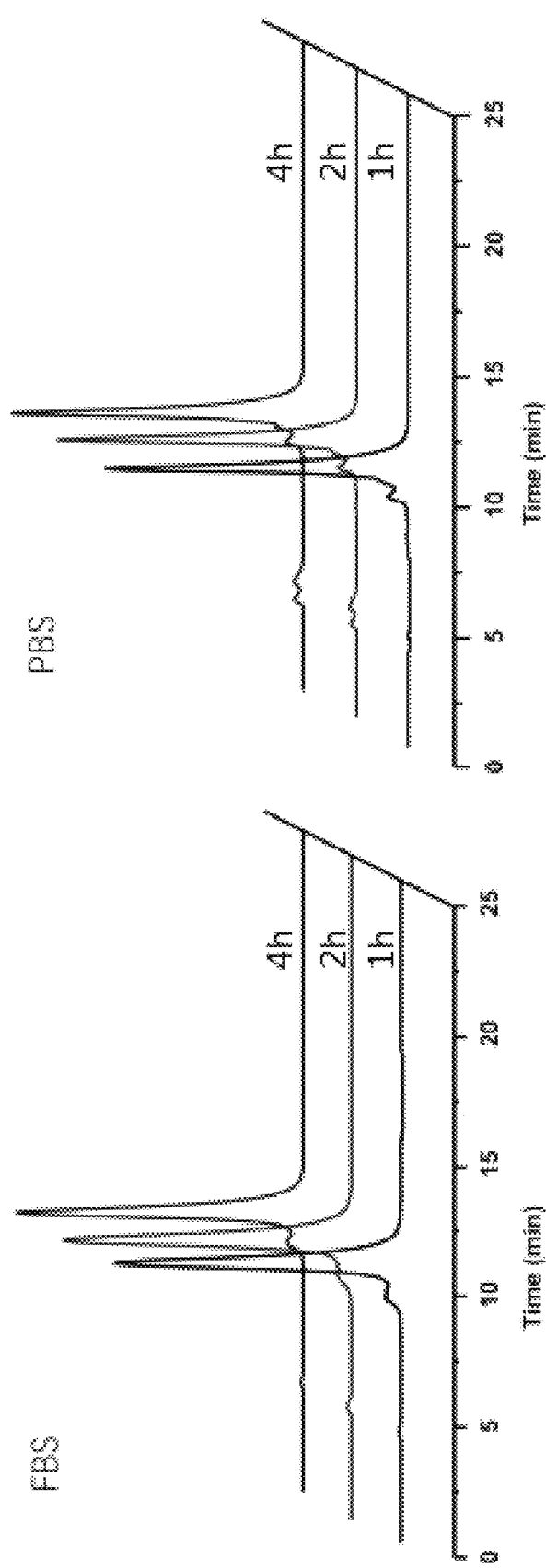
FIG. 4 shows radiochemical purity results of HPLC analysis in Test Example 1.

It can be seen from FIG. 4 that, after the $^{68}$Ga-2PEG(3)-FAPI-dimer is incubated in PBS and FBS, the $^{68}$Ga-2PEG(3)-FAPI-dimer remains intact and is not significantly decomposed, and a radiochemical purity is greater than 90%, indicating that the $^{68}$Ga-2PEG(3)-FAPI-dimer prepared by the present disclosure has excellent stability.

TEST EXAMPLE 2

The radioligand binding research was conducted, including cellular uptake, cellular uptake blockade, and FAP binding assays A human HCC cell line Huh7 was purchased from the National Experimental Cell Resource Sharing Platform, China. CAFs were extracted from a surgical specimen of an HCC patient.

After the CAFs were verified as cells with high FAP expression, the next experiment was conducted. Western Blot was used to determine the FAP expression, and specific steps were as follows: a cell protein was extracted with a lysis buffer (each sample included 20 μg of total protein), separated through sodium dodecyl sulfate-polyacrylamide gel electrophoresis (SDS-PAGE), and transferred to a polyvinylidene fluoride (PVDF) membrane (Millipore), and the PVDF membrane was pre-incubated with a TBST buffer (with 5% skimmed milk) for 1 h and then incubated with a human anti-FAP antibody (ab207178, Abcam); and the PVDF membrane was washed 3 times with TBST and incubated with a horseradish peroxidase (HRP)-labeled secondary antibody, and an enhanced chemiluminescence detection system (C280, Azure) was used for detection. The radioligand binding research was conducted after the CAFs were verified as cells with high FAP expression. The lysis buffer included: 50 mol/L Tris-HCl buffer (pH=8), 150 mmol/L NaCl, 1 mmol/L ethylenediaminetetraacetic acid (EDTA), and 1% (volume fraction) Triton X-100.

FAP-expressing CAFs were inoculated in a 24-well plate and cultivated with a 10% (volume fraction) FBS-containing 1640 medium for 48 h before the experiment until a cell density was about 80% to 90%; the medium was changed to an FBS-free 1640 medium; and the $^{68}$Ga-2PEG(3)-FAPI-dimer, $^{68}$Ga-FAPI-46, or $^{68}$Ga-2PEG(3)-FAPI-dimer+11.3 nmol FAPI-46 (for the blocking experiment) was added to the 24-well plate and incubated, with predetermined intervals of 10 min, 30 min, 60 min, 90 min, and 120 min. The FAP binding assay was conducted after a radiolabeled compound and a corresponding unlabeled FAPI derivative (1.27×10$^{-4}$-10$^{-13}$ mol/L of 2PEG(3)-FAPI-dimer was added to $^{68}$Ga-2PEG(3)-FAPI-dimer; and 2.83×10$^{-4}$-1×10$^{-13}$ mol/L of FAPI-46 was added to $^{68}$Ga-FAPI-46) were co-incubated for 60 min. A half-inhibitory concentration (IC$_{50s}$) was calculated by using GraphPad Prism to fit data through nonlinear regression. In each step of the experiment, cells were washed twice with 1 mL of PBS. Finally, CAFs were lysed with 0.5 mL of a 1 mol/L NaOH aqueous solution to conduct radioactive counting with a gamma counter. 3 parallel replicates were set for each experiment.

Figure 5A:
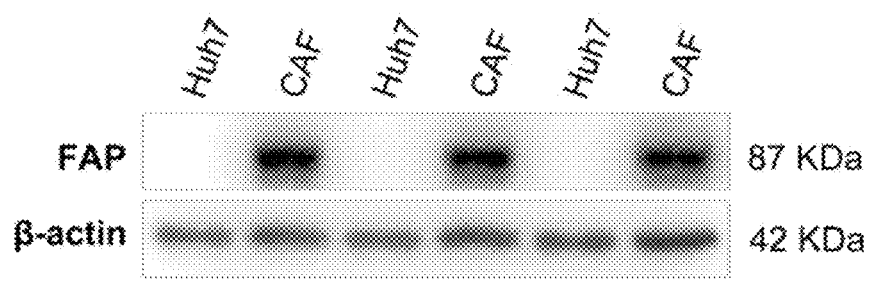
FIG. 5A-D shows assay results of radioligand binding research including cellular uptake, cellular uptake blockade, and FAP binding in Test Example 2, where
Figure 5B:
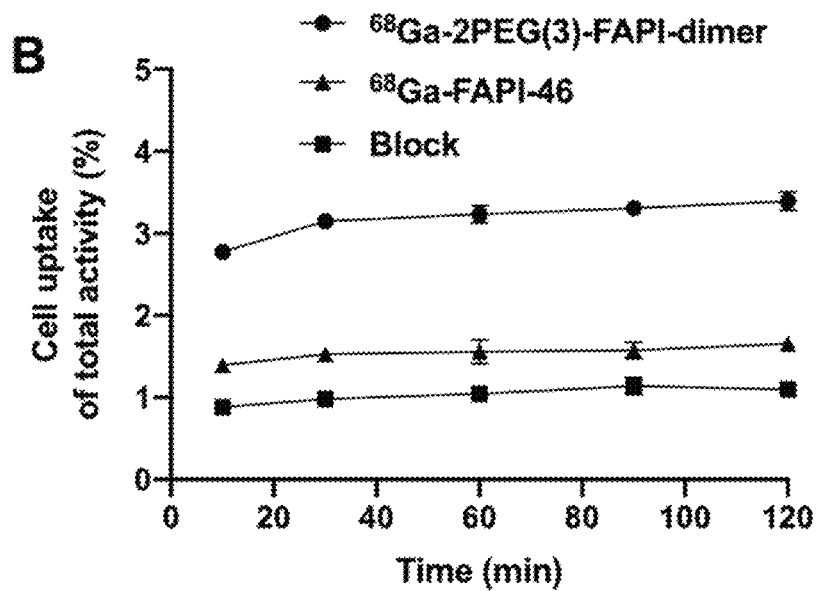

Test results of the radioligand binding research including cellular uptake, cellular uptake blockade, and FAP binding assays were shown in FIG. 5A-B.

FIG. 5A shows the expression of FAP in the liver cancer cell line Huh7 and CAFs, which is determined by Western Blot; and it can be seen from FIG. 5A that CAFs can express FAP at a high level and can be used for subsequent experiments.

FIG. 5B shows the cellular uptake and cellular uptake blockade experiments of $^{68}$Ga-2PEG(3)-FAPI-dimer and $^{68}$Ga-FAPI-46 in CAFs (3 parallel experiments per group). It can be seen from FIG. 5B that the absorption of $^{68}$Ga-FAPI-46 reaches about 1.5% after 10 min of incubation, and is slightly increased before 120 min of incubation; and an absorption mode of $^{68}$Ga-2PEG(3)-FAPI-dimer is similar to that of $^{68}$Ga-FAPI-46, but an absorption value thereof is about twice that of $^{68}$Ga-FAPI-46 monomer. According to results of the cell uptake blockade experiment, the FAPI-46 precursor can significantly block the binding between $^{68}$Ga-2PEG(3)-FAPI-dimer and FAP, indicating that the binding of the $^{68}$Ga-2PEG(3)-FAPI-dimer prepared by the present disclosure to FAP is specific.

Figure 5C:
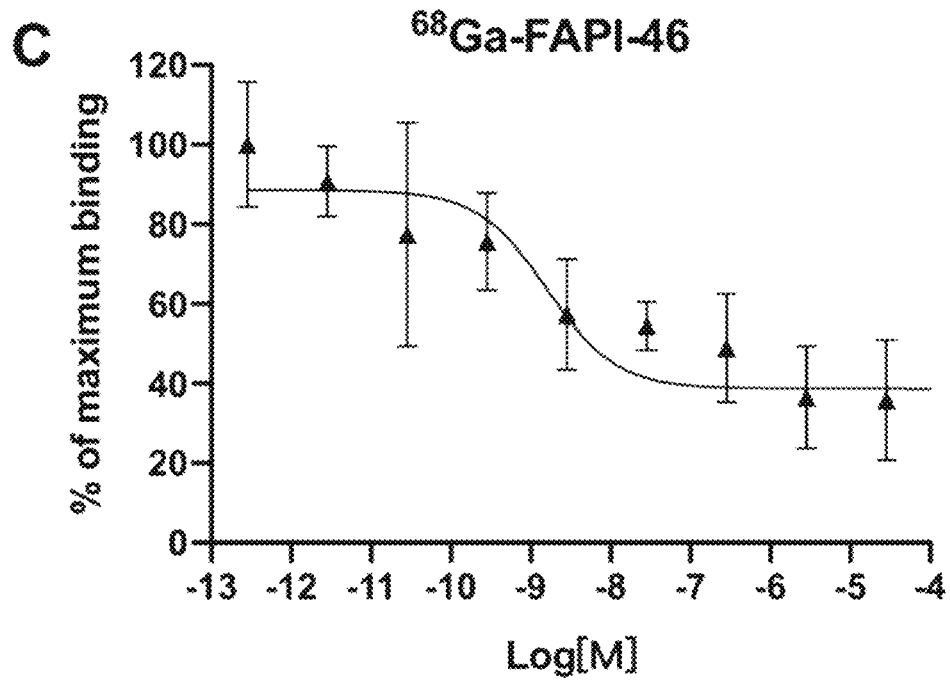

FIG. 5C shows the inhibition of unlabeled FAPI-46 on the binding of $^{68}$Ga-FAPI-46 to FAP on CAFs, and it can be seen from FIG. 5C that an IC$_{50}$ value of $^{68}$Ga-FAPI-46 is 1.60 nmol/L.

Figure 5D:
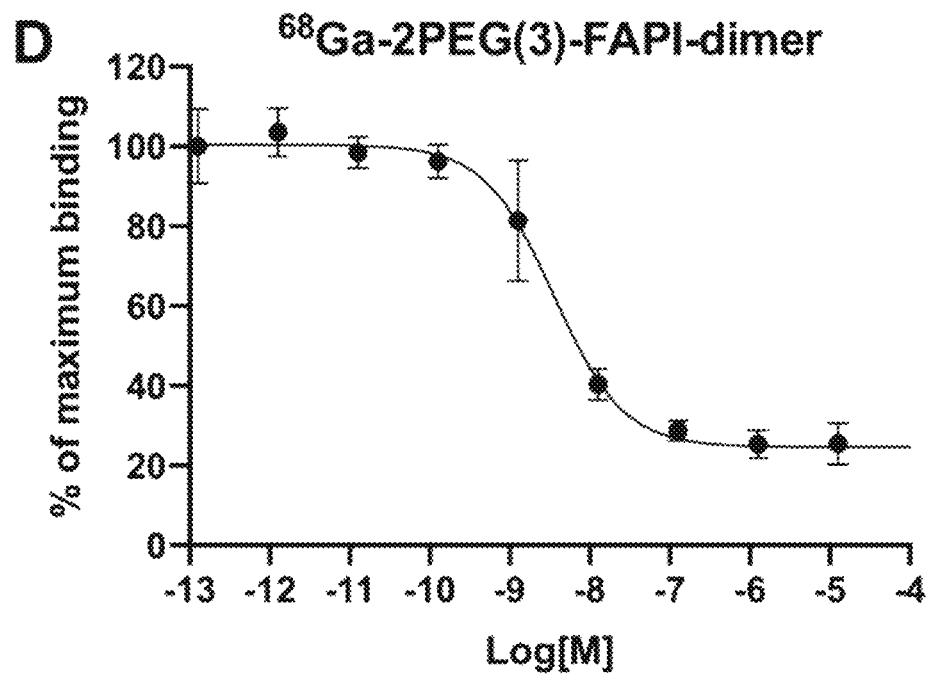

FIG. 5D shows the inhibition of unlabeled 2PEG(3)-FAPI-dimer on the binding of $^{68}$Ga-2PEG(3)-FAPI-dimer to FAP on CAFs, and it can be seen from FIG. 5D that an IC$_{50}$ value of $^{68}$Ga-2PEG(3)-FAPI-dimer is 3.57 nmol/L.

The IC$_{50}$ values of 2PEG(3)-FAPI-dimer and FAPI-46 are similar, indicating that 2PEG(3)-FAPI-dimer has little impact on the binding affinity to a receptor.

TEST EXAMPLE 3

Identification of Human Tumor Tissue-Derived Xenograft (PDX) Models

Figure 6A:
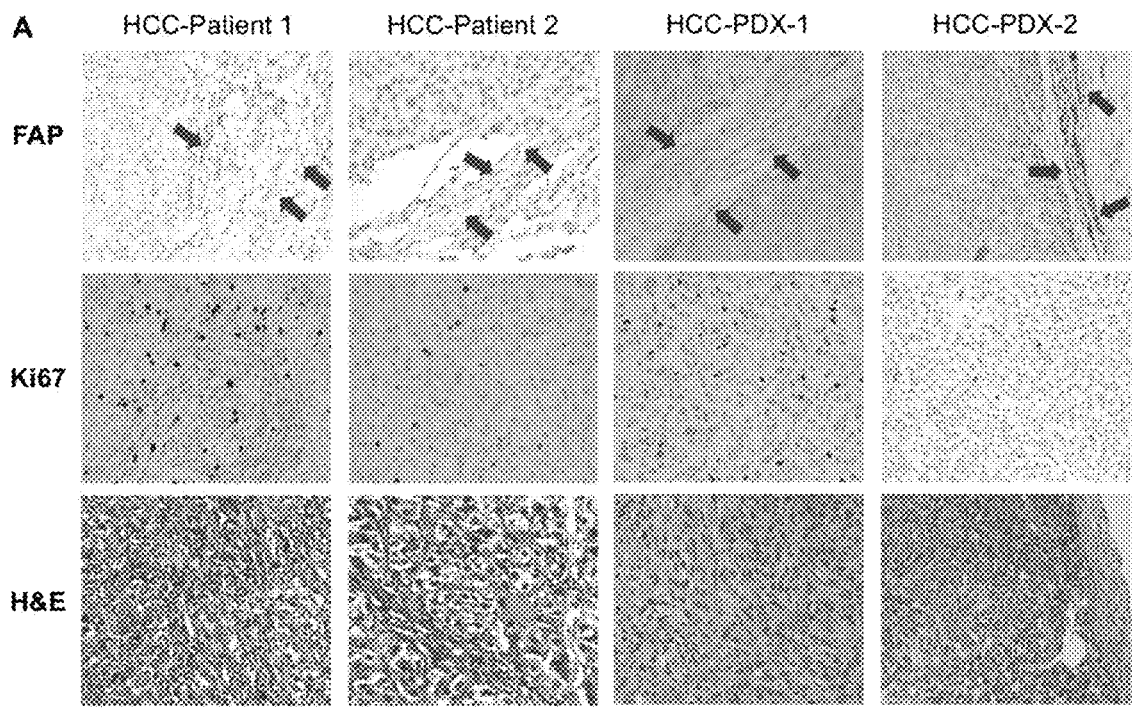
FIG. 6A-B shows the identification results of human tumor tissue-derived xenograft (PDX) models in Test Example 3, where
Figure 6B:
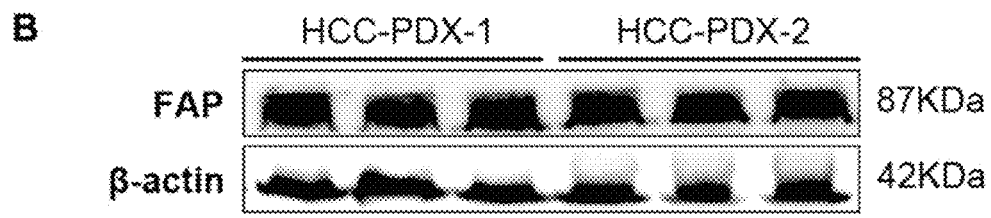

The PET imaging and biodistribution studies were conducted in HCC-PDX1 and HCC-PDX2 mouse models. The histological verification was first conducted, where the immunohistochemical staining and H&E staining were conducted for FAP and Ki67, a tumor tissue was digested for protein extraction, and the expression of FAP was detected by Western Blot. Verification results were shown in FIG. 6A-B, where the immunohistochemical staining result was shown in FIG. 6A and the Western Blot result was shown in FIG. 6B. It can be seen from FIG. 6A-B that FAP and Ki67 immunohistochemical and H&E staining results of HCC-PDX-1 and HCC-PDX-2 are highly consistent with that of the original tumor, and the immunohistochemical staining result indicates FAP-positive expression; and the Western Blot result shows that FAP is expressed at a high level in HCC-PDX-1 and HCC-PDX-2 tumor tissues, indicating FAP-positive expression. Therefore, the models can be used for further mouse experiments.

TEST EXAMPLE 4

PET Imaging Research in HCC-PDX Models

The products of $^{68}$Ga-2PEG(3)-FAPI-dimer and $^{68}$Ga-FAPI-46 were each diluted to a concentration of 74 MBq/mL. 7.4 MBq of $^{68}$Ga-2PEG(3)-FAPI-dimer or 7.4 MBq of $^{68}$Ga-FAPI-46 was injected into the HCC-PDX model through the tail vein (3 parallel experiments per group). All PET scans were conducted with an Inveon small animal PET scanner (Siemens Preclinical Solution, USA). The dynamic PET imaging was conducted with a scan duration of 60 min and reconstructed frames of 10×30 s, 10×60 s, 10×120 s, and 9×160 s. The 10 min static PET imaging was conducted with acquisition time points of 0.5 h, 1 h, 2 h, and 4 h after injection. For the blocking experiment, 30 nmol of unlabeled FAPI-46 was added to a $^{68}$Ga-2PEG(3)-FAPI-dimer solution (with NS as a solvent) before injection. An image was iteratively reconstructed with 3D OPMAP 256.pPetRcn (Siemens) and converted into a % ID/g image. Region of interests (ROIs) in the tumor, liver, heart, kidney, and muscle were calculated on PET images to quantify radioactive signals. Test results were shown in FIG. 7A-B and FIG. 8A-B.

Figure 7A:
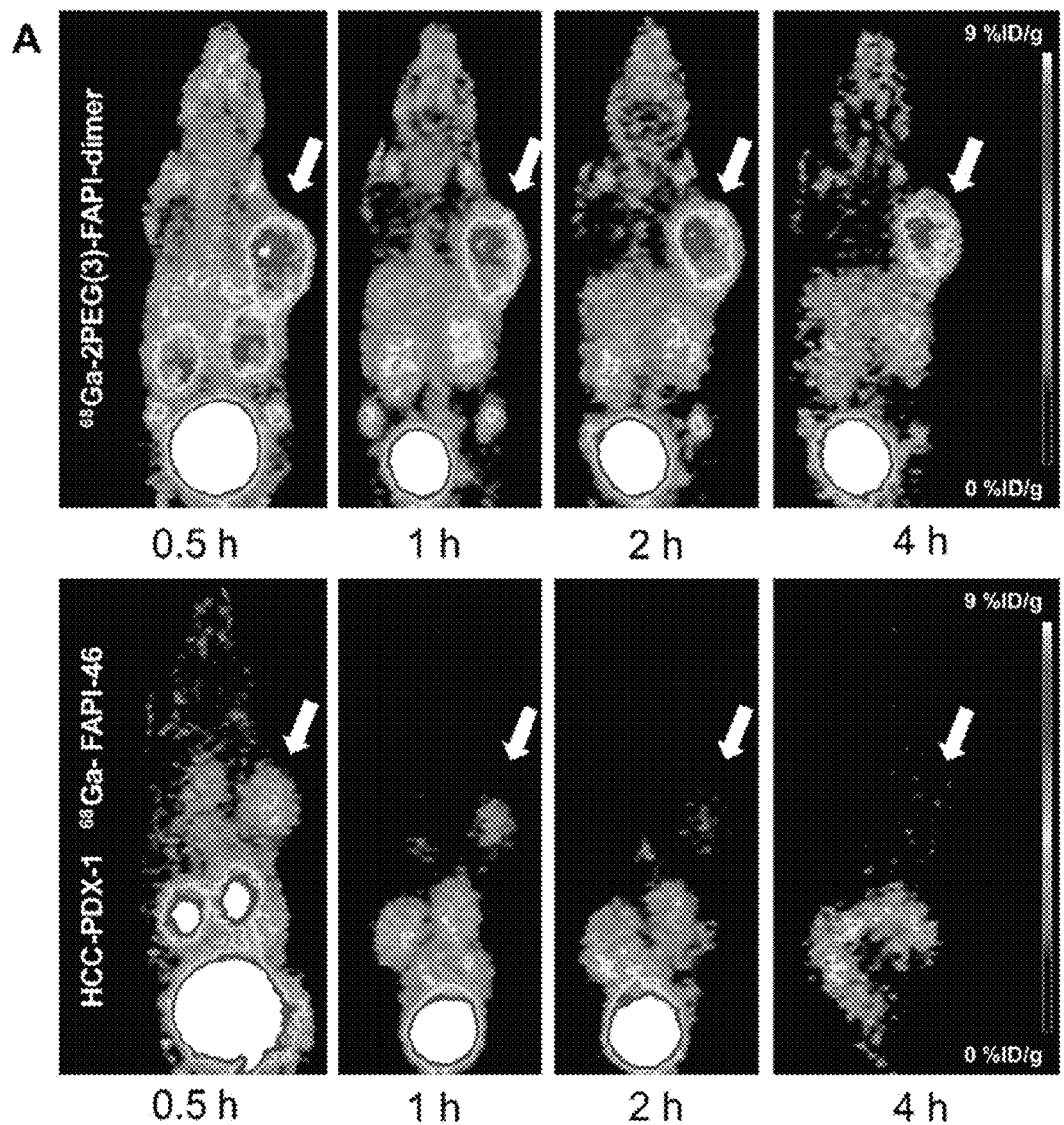
FIG. 7A-B shows the results of PET imaging research in HCC-PDX models in Test Example 4, where
Figure 7B:
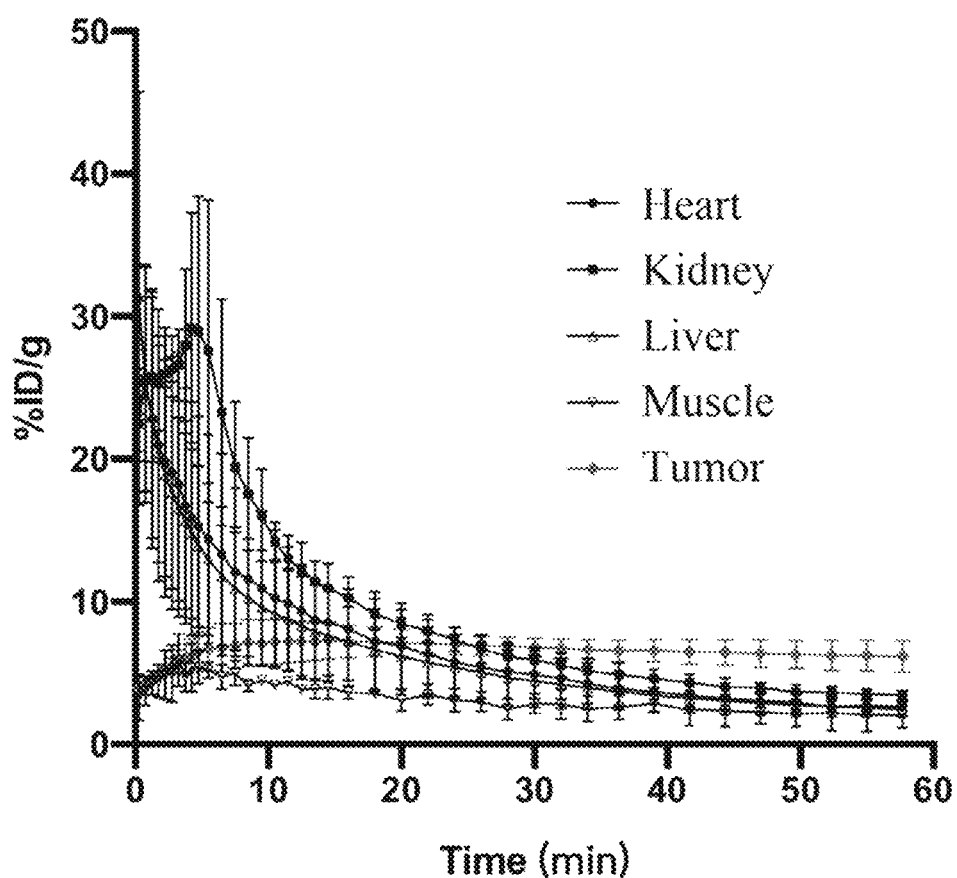

FIG. 7A shows representative static PET images of HCC-PDX-1 at 0.5 h, 1 h, 2 h, and 4 h after the $^{68}$Ga-2PEG(3)-FAPI-dimer and $^{68}$Ga-FAPI-46 are injected, and FIG. 7B shows dynamic time-activity curves of $^{68}$Ga-2PEG(3)-FAPI-dimer in heart, kidney, liver, muscle, and tumor tissues. It can be seen from FIG. 7A-B that the uptake and residence of $^{68}$Ga-2PEG(3)-FAPI-dimer are better than the uptake and residence of $^{68}$Ga-FAPI-46 in a tumor tissue of the HCC-PDX-1 model, and the uptakes of the two in normal organs are low and decline rapidly.

Figure 8A:
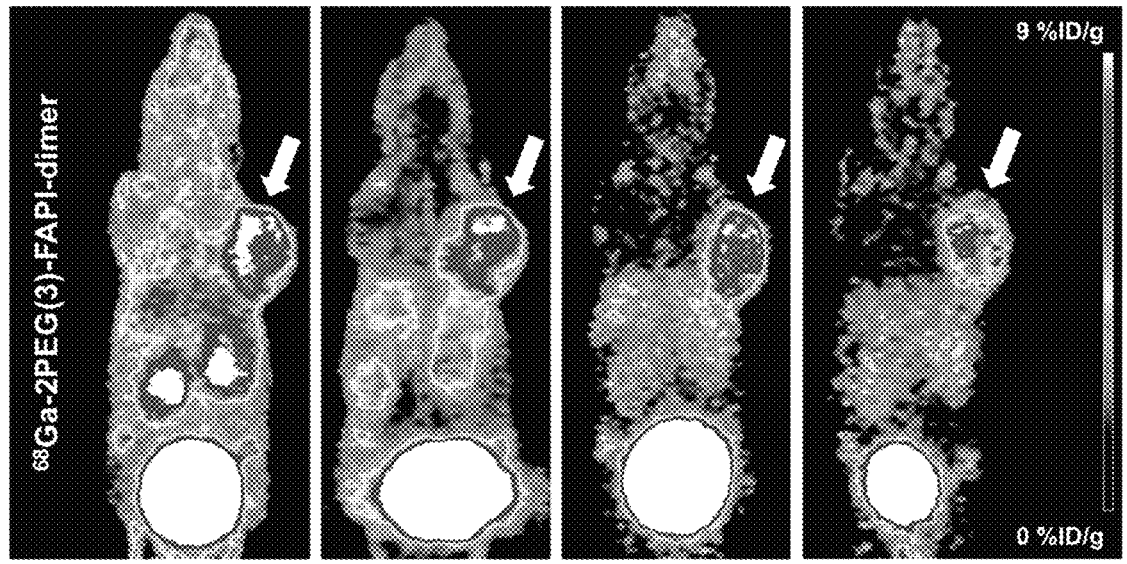
FIG. 8A-B shows the results of PET imaging research in HCC-PDX models in Test Example 4, where
Figure 8A:
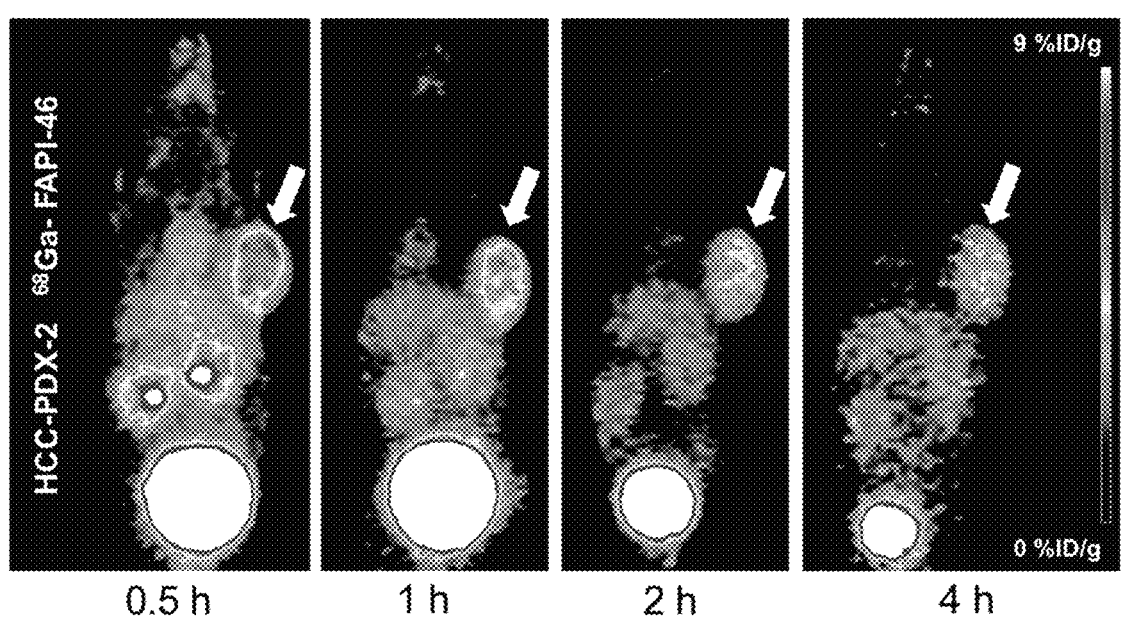
Figure 8B:
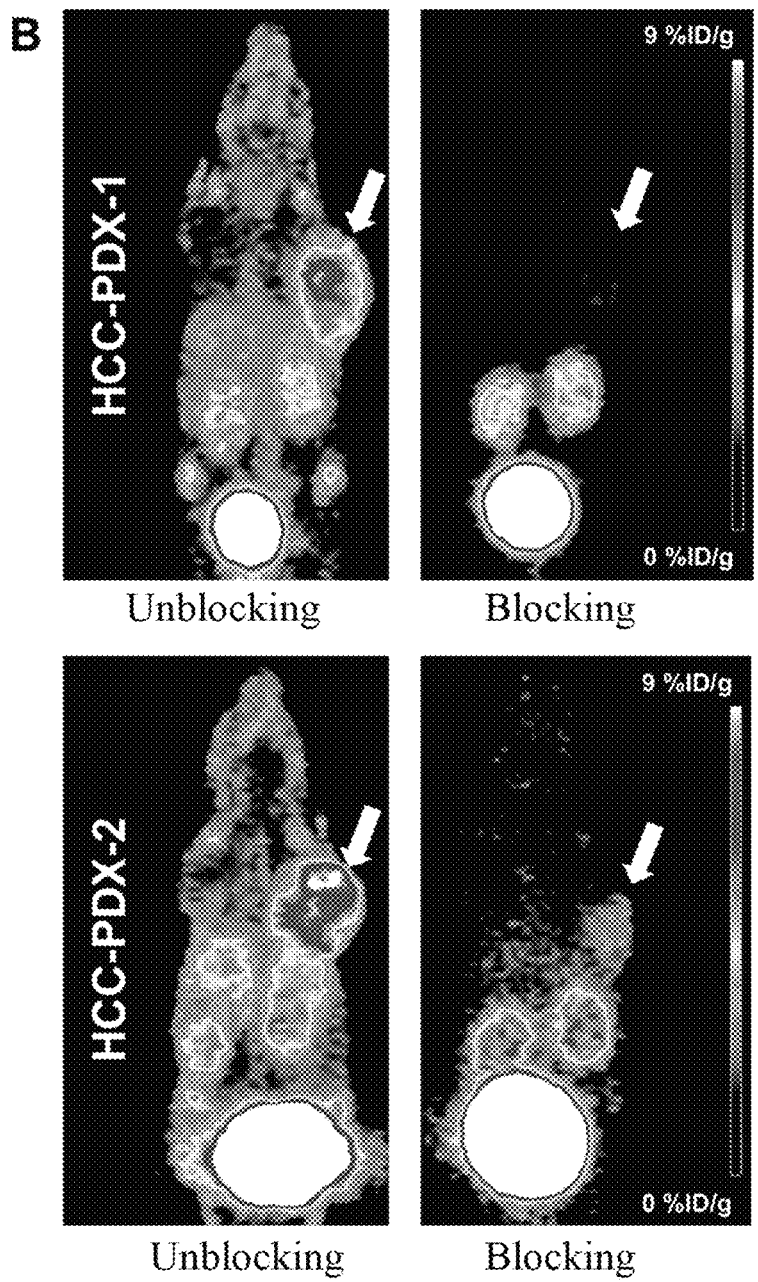

FIG. 8A shows representative static PET images of HCC-PDX-2 at 0.5 h, 1 h, 2 h, and 4 h after the $^{68}$Ga-2PEG(3)-FAPI-dimer and $^{68}$Ga-FAPI-46 are injected and FIG. 8B shows representative static PET images of HCC-PDX-1 and HCC-PDX-2 that are administered with or without a competitive blocker and then injected with $^{68}$Ga-2PEG(3)-FAPI-dimer 1 h later. It can be seen from FIG. 8A-B that the uptake and residence of $^{68}$Ga-2PEG(3)-FAPI-dimer are better than the uptake and residence of $^{68}$Ga-FAPI-46 in a tumor tissue of the HCC-PDX-2 model, and the uptakes of the two in normal organs are low and decline rapidly.

It can be seen from FIG. 7A-B and FIG. 8A-B that, according to the comparison of imaging, uptake, and blocking experimental results of $^{68}$Ga-2PEG(3)-FAPI-dimer and $^{68}$Ga-FAPI-46 in the two liver cancer PDX models, the uptake and residence of $^{68}$Ga-2PEG(3)-FAPI-dimer in a tumor tissue is better than that of $^{68}$Ga-FAPI-46, and can be blocked by unlabeled FAPI-46, indicating that the $^{68}$Ga-2PEG(3)-FAPI-dimer prepared by the present disclosure exhibits prominent specificity in binding to FAP, and its uptake and residence in a tumor are better than that of $^{68}$Ga-FAPI-46.

TEST EXAMPLE 5

Research on Biodistribution of
$^{68}$Ga-2PEG(3)-FAPI-Dimer in the HCC-PDX1
Model In the biodistribution research, a $^{68}$Ga-2PEG(3)-FAPI-dimer solution and a $^{68}$Ga-FAPI-46 solution each had a concentration of 14.8 MBq/mL, where NS was used as a solvent. HCC-PDX-1 mice were injected with 1.48 MBq of $^{68}$Ga-2PEG(3)-FAPI-dimer, and 1 h and 4 h after the injection (3 parallel experiments per time point), major organs and tumors were isolated, weighed, and analyzed. The $^{68}$Ga-FAPI-46 group (1.48 MBq) and blocking group (1.48 MBq $^{68}$Ga-2PEG(3)-FAPI-dimer+30 nmol unlabeled FAPI-46) were compared in terms of biodistribution. The radioactivity (counts per min, cpm) was measured with a gamma counter, and test results were shown in FIG. 9A-B.

Figure 9A:
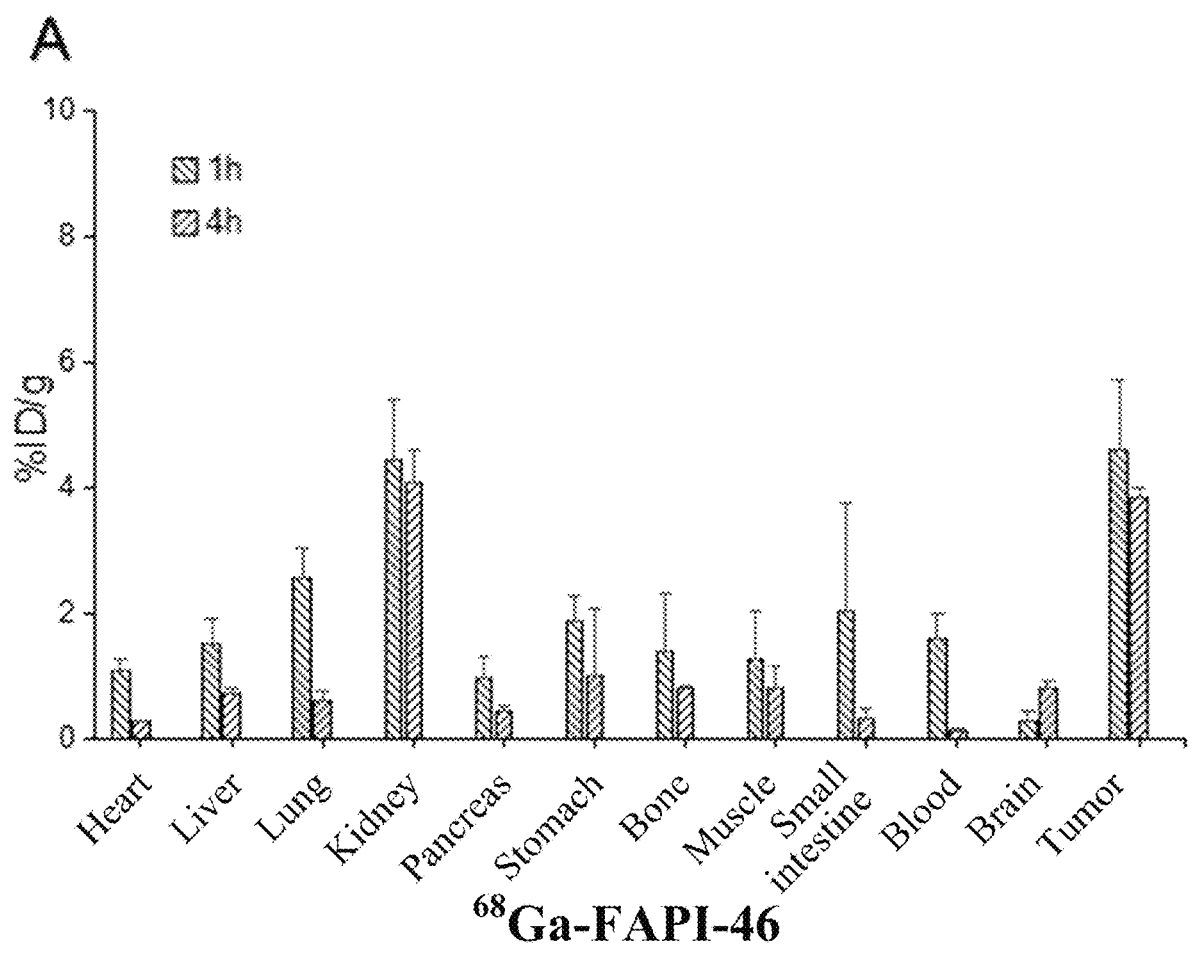
FIG. 9A-B shows the results of biodistribution research of $^{68}$Ga-2PEG(3)-FAPI-dimer in HCC-PDX1 models in Test Example 5, where

FIG. 9A shows the in vitro biodistribution of $^{68}$Ga-FAPI-46 in HCC-PDX-1 at 1 h and 4 h after the injection. It can be seen from FIG. 9A that, 1 h after the injection, the $^{68}$Ga-FAPI-46 is mainly present in the tumor (4.60±1.12% ID/g) and kidney (4.42±0.97% ID/g), with an accumulation ratio of 1.05±0.18 from tumor to kidney (T/K); and 4 h after the injection, $^{68}$Ga-FAPI-46 levels in the blood, heart, liver, lung, and spleen are decreased sharply, while the tumor uptake is stable (3.81±0.18% ID/g).

Figure 9B:
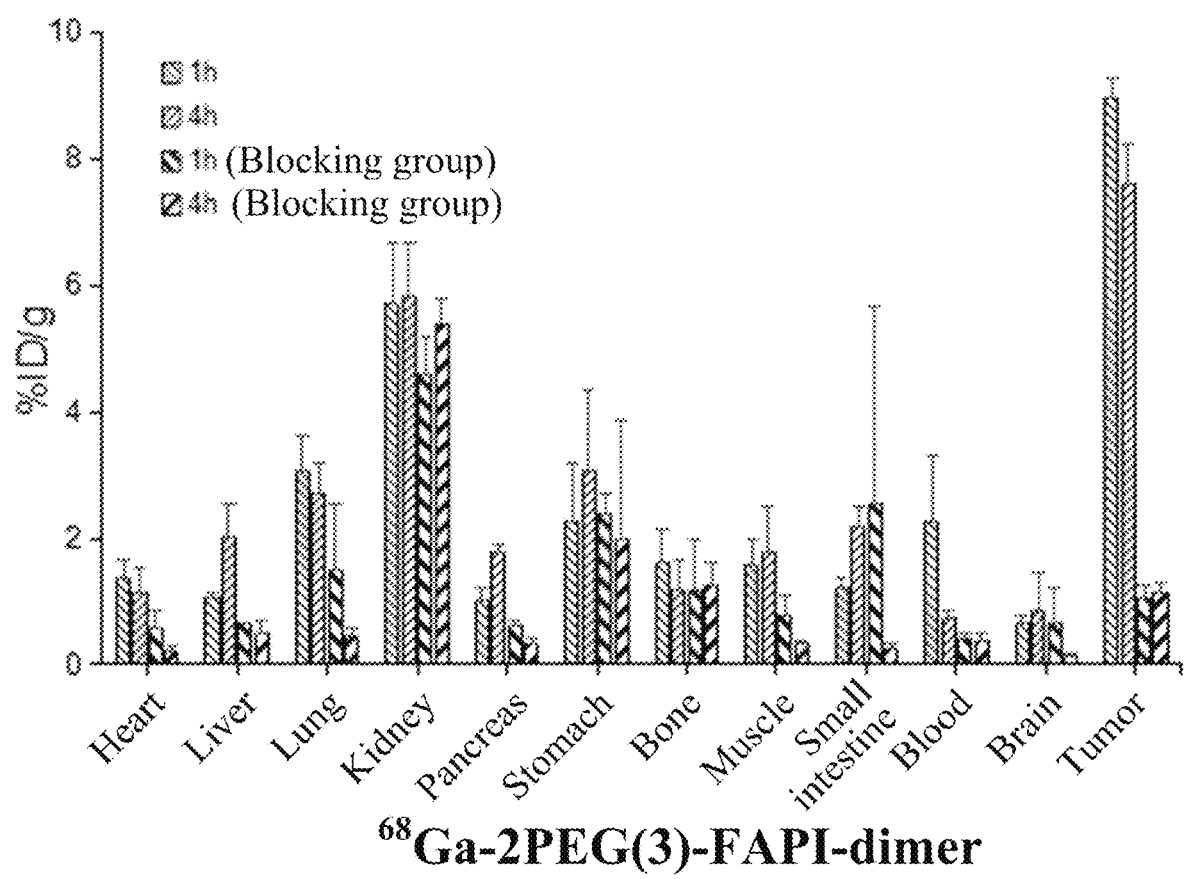
Figure 10A:
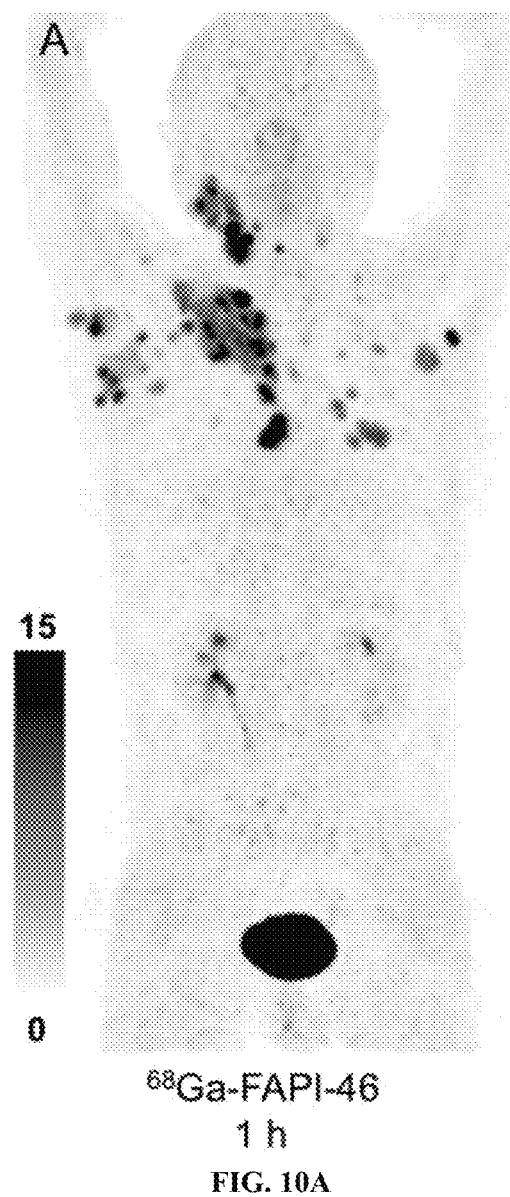
FIG. 10A-D shows the comparison of lesions in a thyroid cancer patient in terms of $^{68}$Ga-FAPI-46 and $^{68}$Ga-2PEG(3)-FAPI-dimer uptake in Test Example 7, where
Figure 10B:
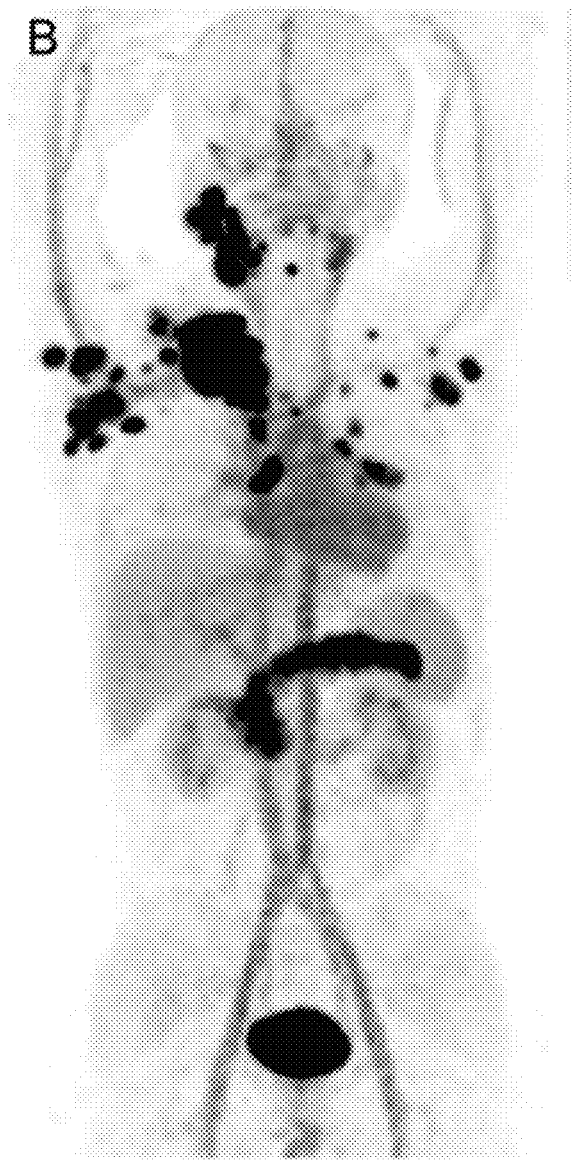
Figure 10C:
Figure 10D:
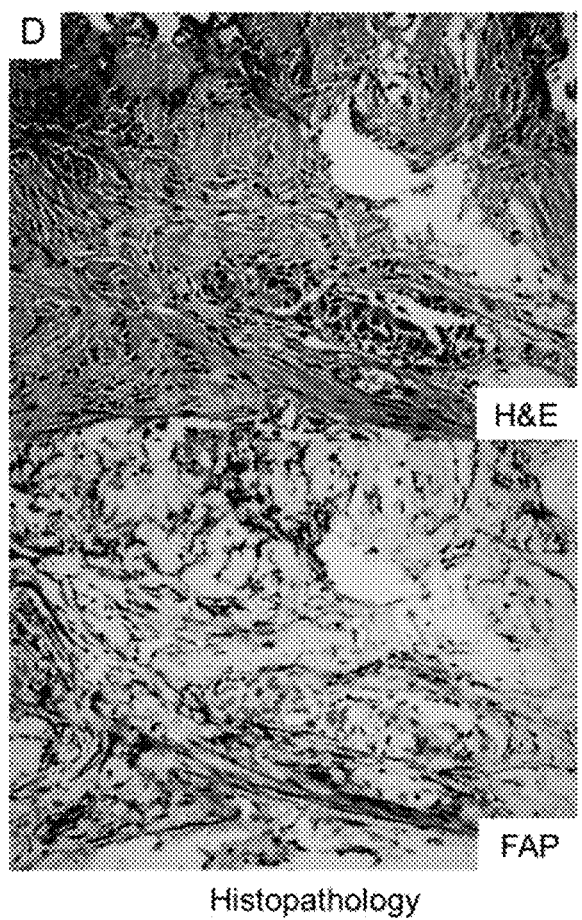

FIG. 9B shows the in vitro biodistribution of $^{68}$Ga-2PEG(3)-FAPI-dimer in HCC-PDX-1 administered with or without unlabeled FAPI-46 as a blocker at 1 h and 4 h after the injection. It can be seen from FIG. 9B that the uptake of $^{68}$Ga-2PEG(3)-FAPI-dimer in the tumor of the HCC-PDX-1 mouse model at 1 h and 4 h is higher than that of the widely-used $^{68}$Ga-FAPI-46 probe. Consistent with the PET imaging findings, the tumor uptakes of $^{68}$Ga-2PEG(3)-FAPI-dimer and $^{68}$Ga-FAPI-46 at 1 h after injection are respectively 8.97±0.32% ID/g and 4.60±1.12% ID/g (P=0.003), and the tumor uptakes at 4 h after injection are respectively 7.61±0.64% ID/g and 3.81±0.18% ID/g (P=0.001), indicating that the $^{68}$Ga-2PEG(3)-FAPI-dimer prepared by the present disclosure exhibits a higher tumor uptake than $^{68}$Ga-FAPI-46. In the blocking group, it is detected that the radioactivity is significantly reduced in most organs, and the reduction in tumor uptake is the most significant (reducing from 8.97±0.32 in the control group to 1.07±0.19% ID/g in the blocking group at 1 h after the injection; and reducing from 7.61±0.64 in the control group to 1.14±0.15% ID/g in the blocking group at 4 h after the injection).

TEST EXAMPLE 6

Research on Distribution of
$^{68}$Ga-2PEG(3)-FAPI-Dimer in Healthy Volunteers

This experiment was approved by the Clinical Research Ethics Committee of the First Affiliated Hospital of Xiamen University, and all subjects signed a written informed consent form. A dose of $^{68}$Ga-2PEG(3)-FAPI-dimer for intravenous injection (1.8 MBq to 2.2 MBq [0.05 mCi to 0.06 mCi]/kg) was calculated according to a body weight of a subject. Data were acquired using a hybrid PET/CT scanner (Discovery MI, GE Healthcare, Milwaukee, WI, USA) at 10 min, 30 min, 60 min, and 180 min after intravenous injection. A maximum standard uptake value (SUVmax) was automatically calculated with ROIs drawn on a transaxial image. Safety data, including vital signs (blood pressure, pulse, respiratory rate, and body temperature) and adverse events, were acquired 4 h before and after the $^{68}$Ga-2PEG(3)-FAPI-dimer was injected. Results showed that a patient did not undergo any discomfort symptoms after the $^{68}$Ga-2PEG(3)-FAPI-dimer was injected. The time-activity curve fitting and subsequent dose calculation were conducted using OLINDA/EXM v.1.1. Dosimetry reports and representative data of three healthy volunteers were shown in Table 2.

TABLE 2

Dosimetry reports and representative data of healthy volunteers

| Main organs | Average value (mSv/MBq) | Standard deviation (SD) (mSv/MBq) |
|---|---|---|
| Adrenal gland | 7.98E−05 | 3.04E−05 |
| Brain | 3.16E−05 | 1.96E−05 |
| Breast | 6.36E−05 | 1.09E−05 |
| Descending colon wall | 9.22E−04 | 2.33E−04 |
| Small intestine | 5.18E−05 | 1.84E−05 |
| Stomach wall | 7.12E−04 | 3.16E−05 |
| Ascending colon wall | 2.79E−05 | 1.13E−05 |
| Kidney | 1.01E−04 | 4.96E−05 |
| Liver | 1.65E−03 | 4.12E−04 |

TABLE 2-continued

Dosimetry reports and representative data of healthy volunteers

| Main organs | Average value (mSv/MBq) | Standard deviation (SD) (mSv/MBq) |
|---|---|---|
| Lung | 1.36E−03 | 4.59E−04 |
| Muscle | 4.19E−05 | 2.07E−05 |
| Ovary | 5.94E−04 | 1.06E−04 |
| Pancreas | 7.61E−04 | 8.05E−04 |
| Red bone marrow | 1.12E−03 | 1.33E−04 |
| Osteoblast | 6.47E−05 | 6.87E−06 |
| Skin | 1.22E−05 | 2.32E−06 |
| Spleen | 1.58E−04 | 9.12E−05 |
| Thymus | 9.64E−06 | 4.47E−06 |
| Thyroid | 3.11E−03 | 4.68E−04 |
| Bladder wall | 1.04E−03 | 5.22E−04 |
| Uterus | 1.27E−05 | 6.00E−06 |
| Effective dose equivalent | 1.69E−02 | 1.92E−03 |
| Effective dose | 1.19E−02 | 9.45E−04 |

It can be seen from Table 2 that an effective dose of the $^{68}$Ga-2PEG(3)-FAPI-dimer is calculated by OLINDA to be 1.19E−02 mSv/MBq (namely, $1.19\times10^{-2}$ mSv/MBq). The organ with the highest effective dose was thyroid (3.11E−03 mSv/MBq), followed by liver (1.65E−03 mSv/MBq) and lung (1.36E−03 mSv/MBq). It indicates that an effective dose of the $^{68}$Ga-2PEG(3)-FAPI-dimer prepared by the present disclosure is comparable to that of $^{68}$Ga-FAPI-02 (1.80E−02 mSv/MBq) and $^{68}$Ga-FAPI-04 (1.64E−02 mSv/MBq), but is higher than that of $^{68}$Ga-FAPI-46 (7.80E−03 mSv/MBq).

TEST EXAMPLE 7

Research of $^{68}$Ga-2PEG(3)-FAPI-Dimer in Tumor Patients

This experiment was approved by the Clinical Research Ethics Committee of the First Affiliated Hospital of Xiamen University, and all subjects signed a written informed consent form. Doses of $^{68}$Ga-FAPI-46 and $^{68}$Ga-2PEG(3)-FAPI-dimer for intravenous injection (1.8 MBq to 2.2 MBq [0.05 mCi to 0.06 mCi]/kg) were calculated according to a body weight of a patient. A cancer patient was administered with $^{68}$Ga-2PEG(3)-FAPI-dimer and $^{68}$Ga-FAPI-46 at an interval of 3 d. Data were acquired using a hybrid PET/CT scanner (Discovery MI, GE Healthcare, Milwaukee, WI, USA). A PET/CT image was acquired at 60 min after intravenous injection (a thyroid cancer patient was scanned twice at 60 min and 240 min after injection). A maximum standard uptake value (SUVmax) was automatically calculated with ROIs drawn on a transaxial image. PET/CT scanning was conducted at 60 min after the three patients were intravenously administered with $^{68}$Ga-FAPI-46 and $^{68}$Ga-2PEG(3)-FAPI-dimer, including a nasopharyngeal carcinoma (NPC) patient (non-keratinizing undifferentiated carcinoma, immunotherapy was conducted when the widespread bone metastasis occurred after chemoradiotherapy), a thyroid cancer patient (multiple cycles of radioactive iodine therapy were conducted after papillary thyroid carcinoma (PTC), total thyroidectomy, and lymph node dissection), and an HCC patient (untreated at preliminary diagnosis). The comparison of $^{68}$Ga-FAPI-46 and $^{68}$Ga-2PEG(3)-FAPI-dimer uptake among lesions in the three cancer patients was shown in Table 3.

TABLE 3

Comparison of $^{68}$Ga-FAPI-46 and $^{68}$Ga-2PEG(3)-FAPI-dimer uptake among lesions in the three cancer patients

| Patient No. | Age | Sex | Preliminary diagnosis/ follow-up diagnosis | Number of lesions | Lesion site | $^{68}$Ga-FAPI-46 SUVmax | $^{68}$Ga-2PEG(3)-FAPI-dimer SUVmax | P |
|---|---|---|---|---|---|---|---|---|
| Patient 1 (NPC) | 71 | Male | Relapse | >10 | Bone metastasis 1 | 16.3 | 17.8 | 0.005 |
| | | | | | Bone metastasis 2 | 24.7 | 27.5 | |
| | | | | | Bone metastasis 3 | 23.4 | 27.4 | |
| | | | | | Bone metastasis 4 | 14.4 | 25.1 | |
| | | | | | Bone metastasis 5 | 22.0 | 29.8 | |
| | | | | | Bone metastasis 6 | 9.8 | 20.8 | |
| | | | | | Bone metastasis 7 | 8.1 | 17.2 | |
| | | | | | Bone metastasis 8 | 13.3 | 22.1 | |
| | | | | | Bone metastasis 10 | 11.6 | 23.3 | |
| Patient 2 (Thyroid cancer) | 34 | Male | Relapse | >10 | Cervical lymph node 1 | 20.0 | 32.8 | 0.005 |
| | | | | | Cervical lymph node 2 | 1.7* | 8.1 | |
| | | | | | Supraclavicular lymph node 1 | 24.0 | 39.0 | |
| | | | | | Supraclavicular lymph node 2 | 12.8 | 24.1 | |
| | | | | | Axillary lymph node 1 | 17.8 | 23.2 | |
| | | | | | Axillary lymph node 2 | 17.7 | 33.2 | |
| | | | | | Axillary lymph node 3 | 16.7 | 28.9 | |
| | | | | | Bone metastasis 1 | 11.4 | 26.4 | |
| | | | | | Mediastinal lymph node 1 | 23.4 | 24.6 | |
| | | | | | Hilar lymph node 1 | 11.5 | 18.1 | |
| Patient 3 (HCC) | 46 | Male | Preliminary diagnosis | 1 | Primary tumor | 2.7 | 9.8 | NA |

It can be seen from Table 3 that, in the comparative analysis of single lesions, the uptake of $^{68}$Ga-2PEG(3)-FAPI-dimer is significantly higher than the uptake of $^{68}$Ga-FAPI-46.

FIG. 10A-D shows the comparison of lesions in the thyroid cancer patient in terms of $^{68}$Ga-FAPI-46 and $^{68}$Ga-2PEG(3)-FAPI-dimer uptake, where A shows a result at 1 h after the $^{68}$Ga-FAPI-46 is injected, B shows a result at 1 h after the $^{68}$Ga-2PEG(3)-FAPI-dimer is injected, C shows a result at 4 h after the $^{68}$Ga-2PEG(3)-FAPI-dimer is injected, and D shows a result of puncture of metastatic lymph nodes. It can be seen from FIG. 10A-D that the $^{68}$Ga-2PEG(3)-FAPI-dimer in the thyroid cancer patient mainly accumulates in the tumor, pancreas, submandibular gland, and blood pool. All tumor lesions can be clearly visualized due to a prominent tumor-to-background ratio. At 1 h after injection, the uptake of $^{68}$Ga-2PEG(3)-FAPI-dimer in a lesion ranges from 8.1 to 39.0, while the uptake of $^{68}$Ga-FAPI-46 ranges from 1.7 to 24.0. In addition, the uptake of $^{68}$Ga-2PEG(3)-FAPI-dimer in a tumor is only slightly decreased from 1 h to 4 h (maximum standard uptake value [SUVmax] at 1 h: 8.1 to 39.0; and SUVmax at 4 h: 6.6 to 35.0). The metastatic lymph nodes were punctured to allow H&E staining and immunohistochemical staining. An H&E staining result showed that CAFs were abundant in a tumor tissue, and an FAP immunohistochemical staining result showed that FAP was strongly expressed.

Figure 11A:
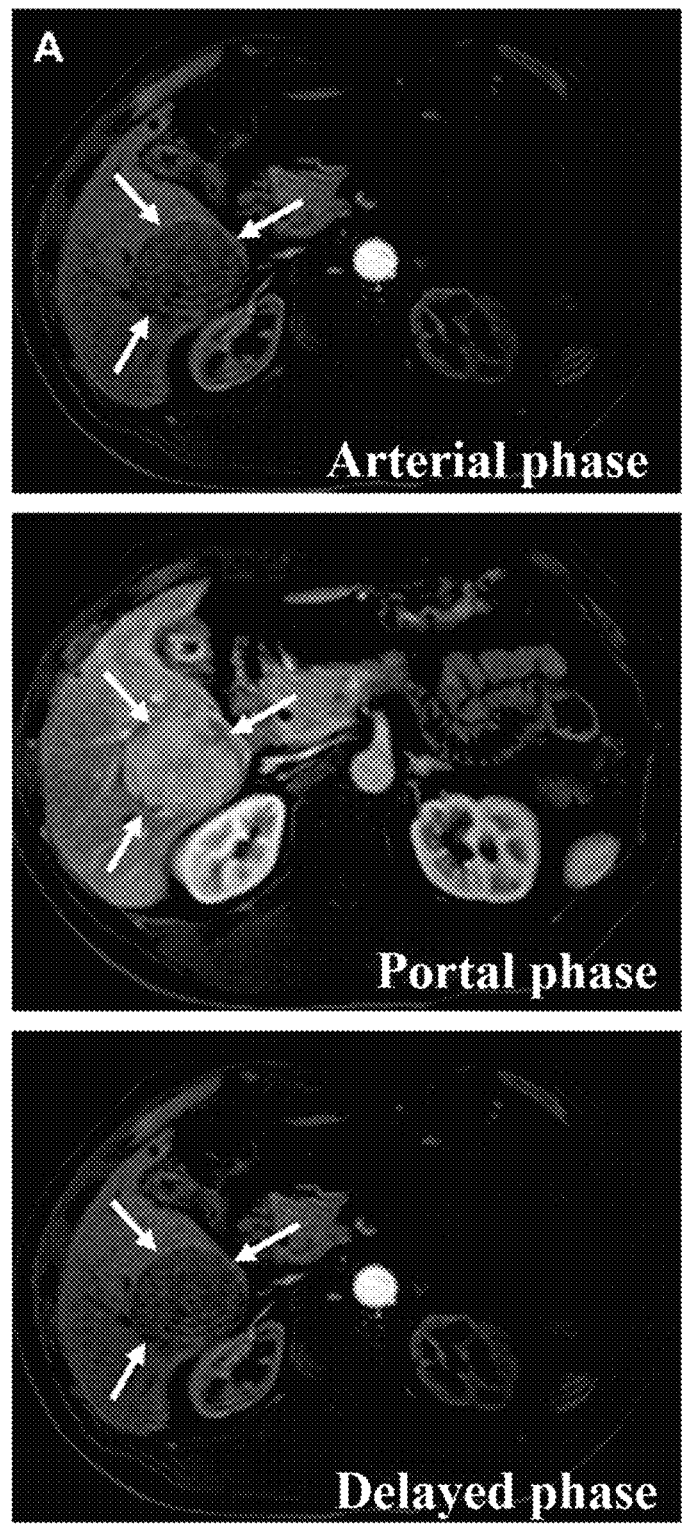
FIG. 11A-C shows the comparison of lesions in an HCC patient in terms of $^{68}$Ga-FAPI-46 and $^{68}$Ga-2PEG(3)-FAPI-dimer uptake in Test Example 7, where
Figure 11B:
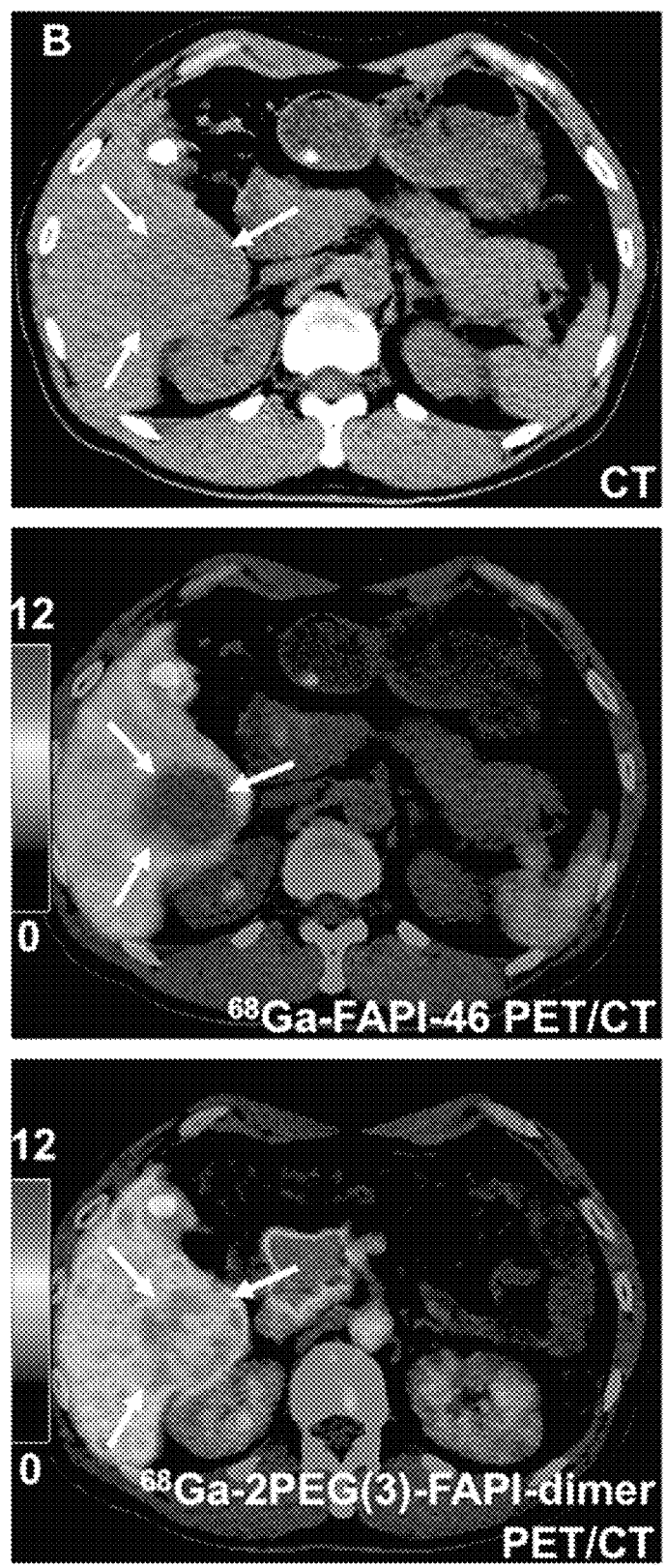
Figure 11C:
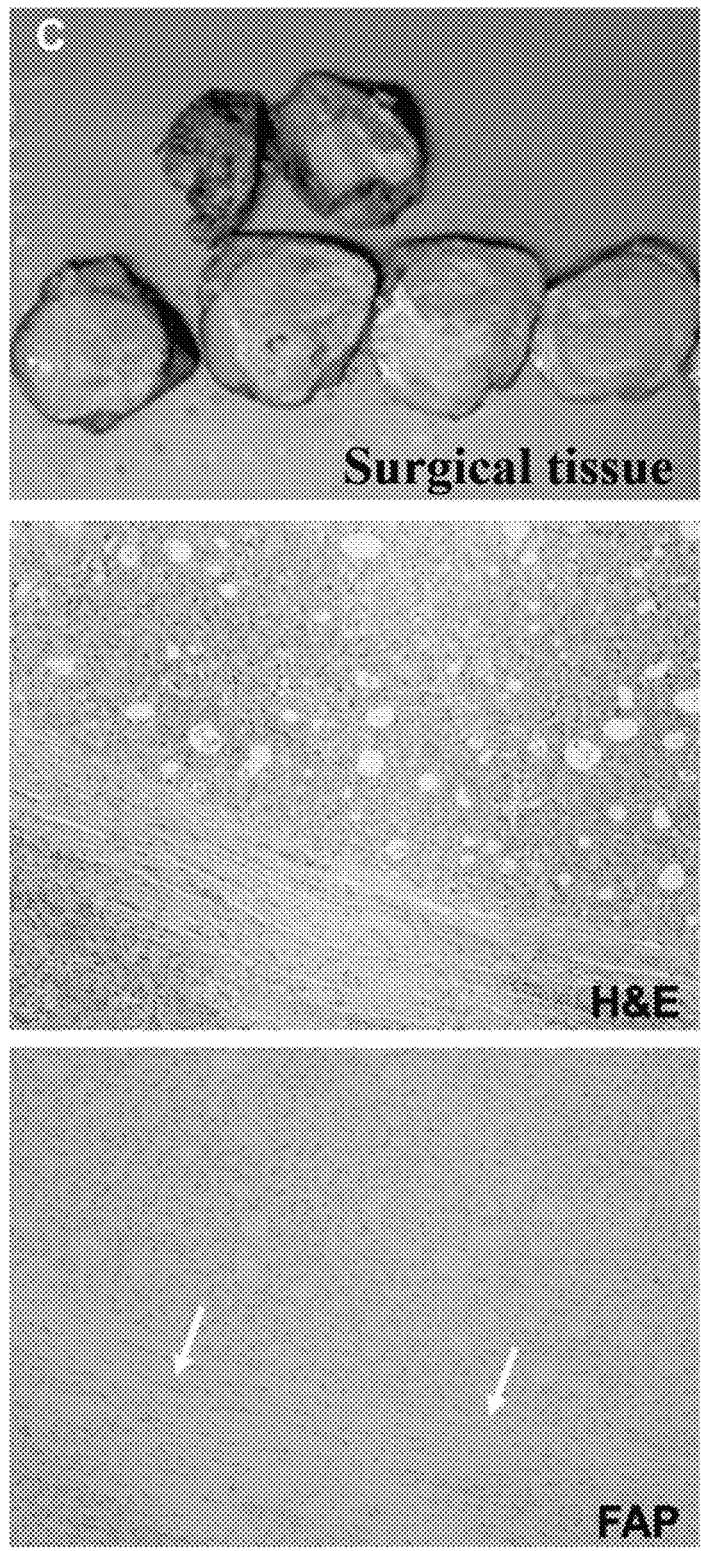

FIG. 11A-C shows the comparison of lesions in the HCC patient in terms of $^{68}$Ga-FAPI-46 and $^{68}$Ga-2PEG(3)-FAPI-dimer uptake, where A shows enhanced MRI images, B shows a CT image and PET/CT images at 1 h after the $^{68}$Ga-FAPI-46 and $^{68}$Ga-2PEG(3)-FAPI-dimer are administered, and C shows surgical tissue, H&E staining, and FAP immunohistochemical staining results. It can be seen from FIG. 11A-C that the uptake of $^{68}$Ga-FAPI-46 in the lesions is low (SUVmax 2.7), while the uptake of $^{68}$Ga-2PEG(3)-FAPI-dimer in the lesions is high (SUVmax 9.8) (which is higher than that in the surrounding liver tissues, resulting in a prominent target-to-background ratio); and the surgical tissue, H&E staining, and FAP immunohistochemical staining results indicate that FAP is expressed at a low level in the tumor stroma. It indicates that the $^{68}$Ga-2PEG(3)-FAPI-dimer prepared by the present disclosure exhibits better tumor uptake than $^{68}$Ga-FAPI-46 even in a tumor with low expression.

The above descriptions are merely preferred implementations of the present disclosure. It should be noted that a person of ordinary skill in the art may further make several improvements and modifications without departing from the principle of the present disclosure, but such improvements and modifications should be deemed as falling within the protection scope of the present disclosure.

What is claimed is:

1. A preparation method of a fibroblast activation protein inhibitor (FAPI) dimer compound with a structure shown in formula I:

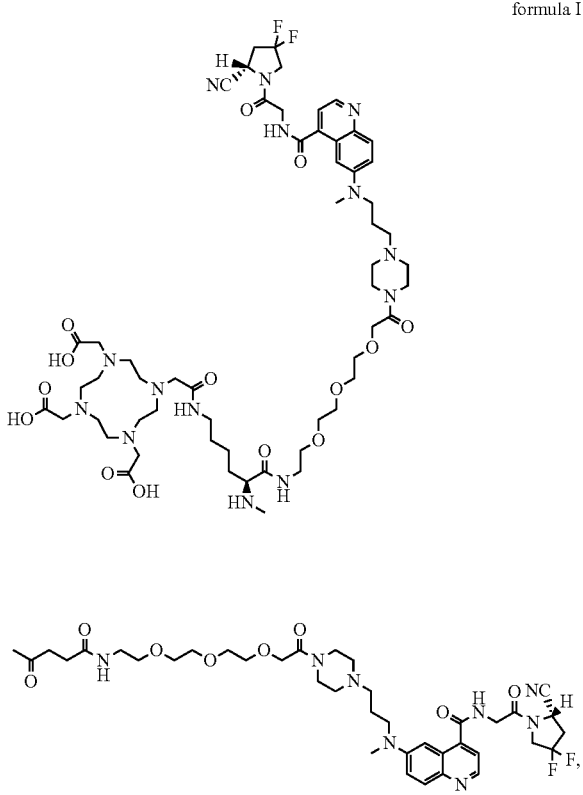

formula I the preparation method comprising the following steps:

(1) mixing a compound 1, a compound 2, a first condensation reagent, and a first organic base to allow a first condensation reaction, and subjecting a resulting condensation product to a first Boc protecting group removal reaction to obtain a compound 3;

(2) mixing the compound 3, a compound 4, a second condensation reagent, and a second organic base to allow a second condensation reaction, and subjecting a resulting condensation product to a second Boc protecting group removal reaction to obtain a compound 5;

(3) mixing the compound 5, a compound 6, a third condensation reagent, and a third organic base to allow a third condensation reaction, and subjecting a resulting condensation product to an Fmoc protecting group removal reaction to obtain a compound 7; and (4) mixing the compound 7, a compound 8, a fourth condensation reagent, and a fourth organic base to allow a fourth condensation reaction, and subjecting a resulting condensation product to a carboxylic acid protecting group removal reaction to obtain the FAPI dimer compound with a structure shown in formula I;

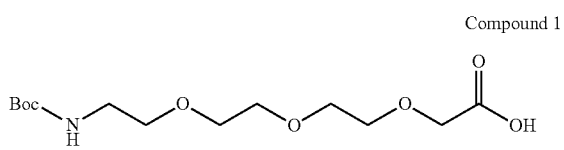

Compound 1

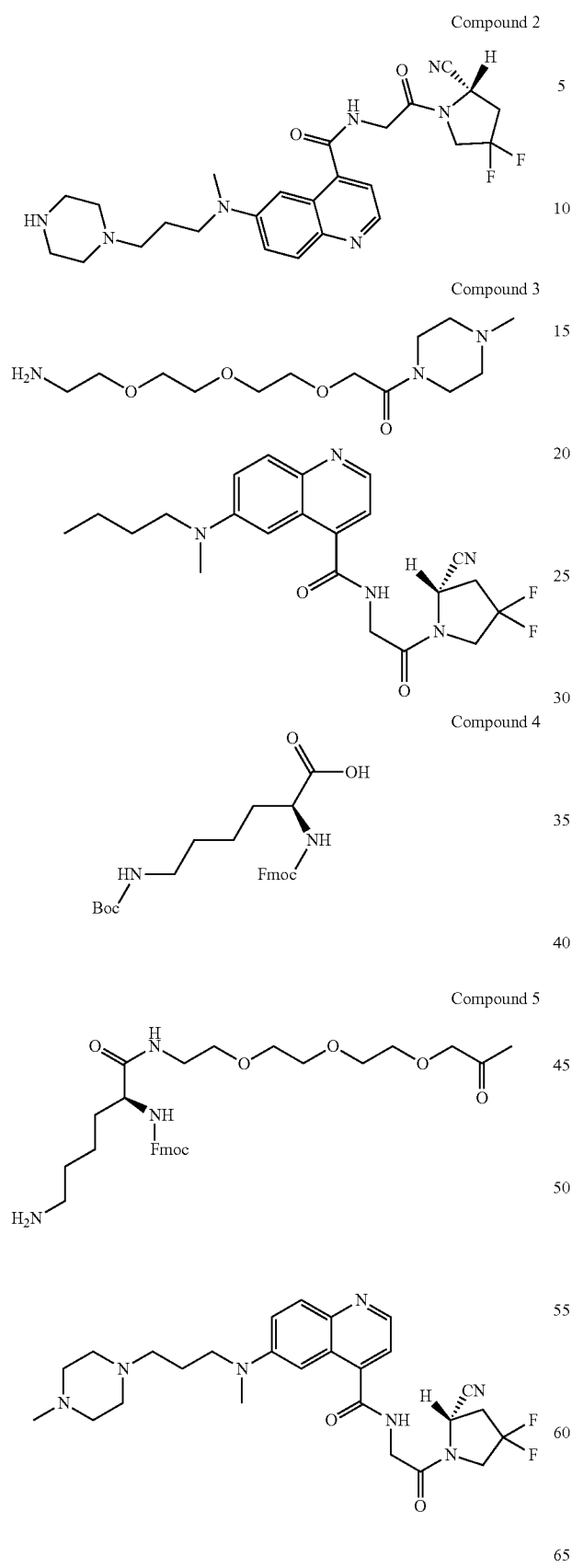
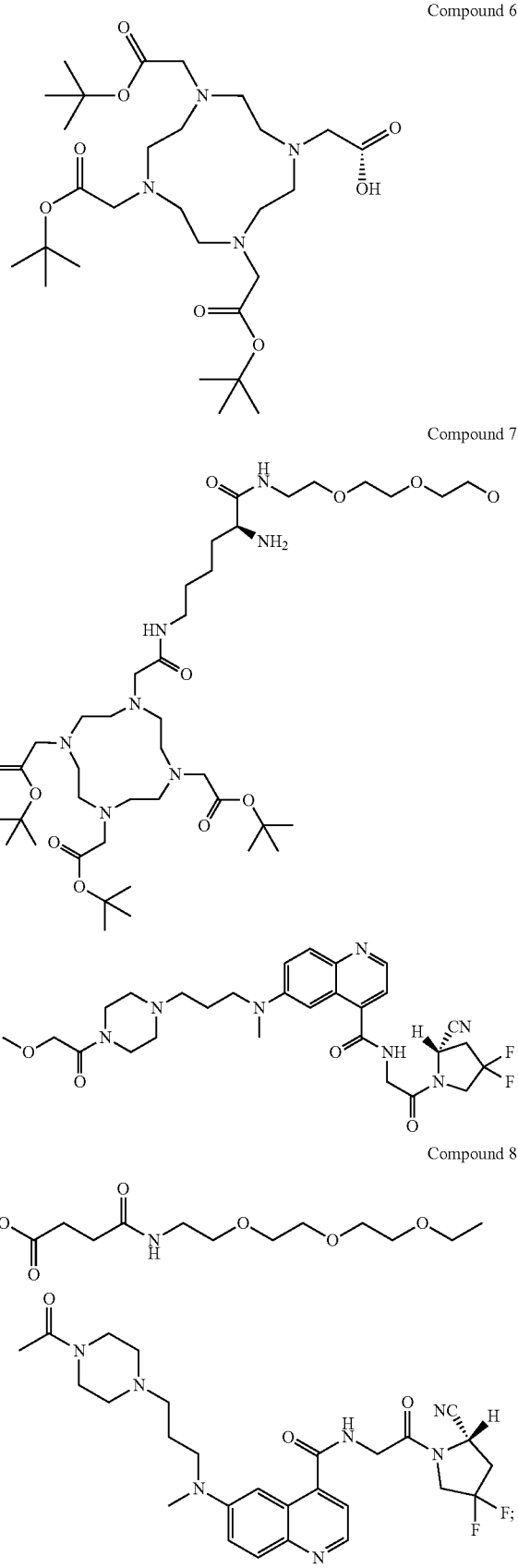

wherein in step (2), the compound 3, the compound 4, the second condensation reagent, and the second organic base are in a molar ratio of 1:(1-5):(1-5):(2-6);

the second condensation reaction is conducted at 25° C. to 100° C. for 4 h to 16 h; and the second Boc protecting group removal reaction is conducted at 0° C. to 50° C. for 0.5 h to 3 h; and wherein in step (3), the compound 5, the compound 6, the third condensation reagent, and the third organic base are in a molar ratio of 1:(1-3):(2-6):(5-10);

the third condensation reaction is conducted at 25° C. to 100° C. for 4 h to 16 h; and the Fmoc protecting group removal reaction is conducted at 0° C. to 50° C. for 0.5 h to 3 h.

2. The preparation method according to claim 1, wherein in step (1), the compound 2, the compound 1, the first condensation reagent, and the first organic base are in a molar ratio of 1:(1-5):(1-5):(2-6);

the first condensation reaction is conducted at 25° C. to 100° C. for 4 h to 16 h; and the first Boc protecting group removal reaction is conducted at 0° C. to 50° C. for 0.5 h to 5 h.

3. The preparation method according to claim 2, wherein the first condensation reagent, the second condensation reagent, the third condensation reagent, and the fourth condensation reagent each independently comprise one or more selected from the group consisting of 2-(7-azabenzotriazole)-N,N,N',N'-tetramethyluronium hexafluorophosphate (HATU), O—(N-succinimidyl)-N,N,N',N'-tetramethyluronium tetrafluoroborate (TSTU), and O-benzotriazole-tetramethyluronium hexafluorophosphate (HBTU); and the first organic base, the second organic base, the third organic base, and the fourth organic base each independently comprise an organic amine and/or 4-dimethylaminopyridine (4-DMAP).

4. The preparation method according to claim 1, wherein in step (4), the compound 7, the compound 8, the fourth condensation reagent, and the fourth organic base are in a molar ratio of 1:(1-5):(2-6):(5-10);

the fourth condensation reaction is conducted at 25° C. to 100° C. for 1 h to 10 h; and the carboxylic acid protecting group removal reaction is conducted at 0° C. to 50° C. for 0.5 h to 5 h.

5. The preparation method according to claim 4, wherein the first condensation reagent, the second condensation reagent, the third condensation reagent, and the fourth condensation reagent each independently comprise one or more selected from the group consisting of 2-(7-azabenzotriazole)-N,N,N',N'-tetramethyluronium hexafluorophosphate (HATU), O—(N-succinimidyl)-N,N,N',N'-tetramethyluronium tetrafluoroborate (TSTU), and O-benzotriazole-tetramethyluronium hexafluorophosphate (HBTU); and the first organic base, the second organic base, the third organic base, and the fourth organic base each independently comprise an organic amine and/or 4-dimethylaminopyridine (4-DMAP).

6. The preparation method according to claim 1, wherein the first condensation reagent, the second condensation reagent, the third condensation reagent, and the fourth condensation reagent each independently comprise one or more selected from the group consisting of 2-(7-azabenzotriazole)-N,N,N',N'-tetramethyluronium hexafluorophosphate (HATU), O—(N-succinimidyl)-N,N,N',N'-tetramethyluronium tetrafluoroborate (TSTU), and O-benzotriazole-tetramethyluronium hexafluorophosphate (HBTU); and the first organic base, the second organic base, the third organic base, and the fourth organic base each independently comprise an organic amine and/or 4-dimethylaminopyridine (4-DMAP).

* * * * *